US009603569B2

(12) United States Patent
Mirov et al.

(10) Patent No.: US 9,603,569 B2
(45) Date of Patent: Mar. 28, 2017

(54) POSITIONING A WEARABLE DEVICE FOR DATA COLLECTION

(71) Applicant: Verily Life Sciences LLC, Mountain View, CA (US)

(72) Inventors: Russell Norman Mirov, Los Altos, CA (US); Andrew Homyk, Belmont, CA (US); Mark West Askew, San Francisco, CA (US); Jason Donald Thompson, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 172 days.

(21) Appl. No.: 14/329,341

(22) Filed: Jul. 11, 2014

(65) Prior Publication Data

US 2016/0007925 A1 Jan. 14, 2016

(51) Int. Cl.
*A61B 5/00* (2006.01)
*G01B 11/14* (2006.01)

(52) U.S. Cl.
CPC ............ *A61B 5/681* (2013.01); *A61B 5/0059* (2013.01); *A61B 5/489* (2013.01); *A61B 5/70* (2013.01); *G01B 11/14* (2013.01); *A61B 5/0022* (2013.01)

(58) Field of Classification Search
CPC ......... A61B 5/68; A61B 5/684; A61B 5/6841; A61B 5/6842; A61B 5/6843; A61B 5/6844; A61B 5/4887; A61B 5/489; A61B 5/4893; A61B 5/4896; A61B 5/0059; A61B 5/0062; A61B 5/0064; A61B 5/0066; A61B 5/0068; A61B 5/0075; A61B 5/0077; A61B 5/0079; A61B 5/0082; A61B 5/0015; A61B 5/0017; A61B 5/002; A61B 5/0022; A61B 5/0024;

(Continued)

(56) References Cited

U.S. PATENT DOCUMENTS 5,642,733 A * 7/1997 Archibald ............ A61B 5/6833
600/481
8,652,040 B2 2/2014 LeBoeuf et al.
(Continued)

FOREIGN PATENT DOCUMENTS

WO 2013/076656 A1 5/2013

OTHER PUBLICATIONS

International Search Report and Written Opinion of International Application No. PCT/US2015/039659, dated Oct. 29, 2015.

*Primary Examiner* — Gordon J Stock, Jr.
(74) *Attorney, Agent, or Firm* — McDonnell Boehnen Hulbert & Berghoff LLP

(57) ABSTRACT

Wearable devices are described herein including at least two photodetectors and a mount configured to mount the at least two photodetectors to an external surface of a wearer. The at least two photodetectors are configured to detect alignment between the wearable device and a target on or in the body of the wearer (e.g., to detect the location of vasculature within the body of the wearer relative to the at least two photodetectors). Alignment of the at least two photodetectors relative to the target could enable detection of one or more physiological properties of the wearer. For example, the wearable device could include a sensor configured to detect a property of the target when the sensor is above the target, and alignment of the target relative to the at least two photodetectors could include the sensor being located above the target.

18 Claims, 9 Drawing Sheets

(58) Field of Classification Search
CPC ......... G01B 11/14; G01B 11/26; G01B 11/27; G01B 11/272
See application file for complete search history.

(56) References Cited

U.S. PATENT DOCUMENTS

| | | |
|---|---|---|
| 8,708,904 B2 | 4/2014 | Stivoric et al. |
| 2002/0188210 A1 | 12/2002 | Aizawa |
| 2005/0054907 A1 | 3/2005 | Page et al. |
| 2006/0258939 A1 | 11/2006 | Pesach et al. |
| 2007/0085995 A1* | 4/2007 | Pesach ............... A61B 5/14532 356/39 |
| 2007/0093717 A1* | 4/2007 | Nagar ................... A61B 5/0095 600/438 |
| 2008/0081968 A1 | 4/2008 | Numada et al. |
| 2010/0210956 A1 | 8/2010 | Im |
| 2013/0144176 A1* | 6/2013 | Lec ...................... A61B 5/0002 600/485 |
| 2013/0184544 A1 | 7/2013 | Su et al. |
| 2014/0107493 A1 | 4/2014 | Yuen et al. |
| 2014/0364749 A1* | 12/2014 | Varma ...................... A61B 5/22 600/494 |
| 2015/0157220 A1* | 6/2015 | Fish ................... A61B 5/02055 600/301 |

\* cited by examiner

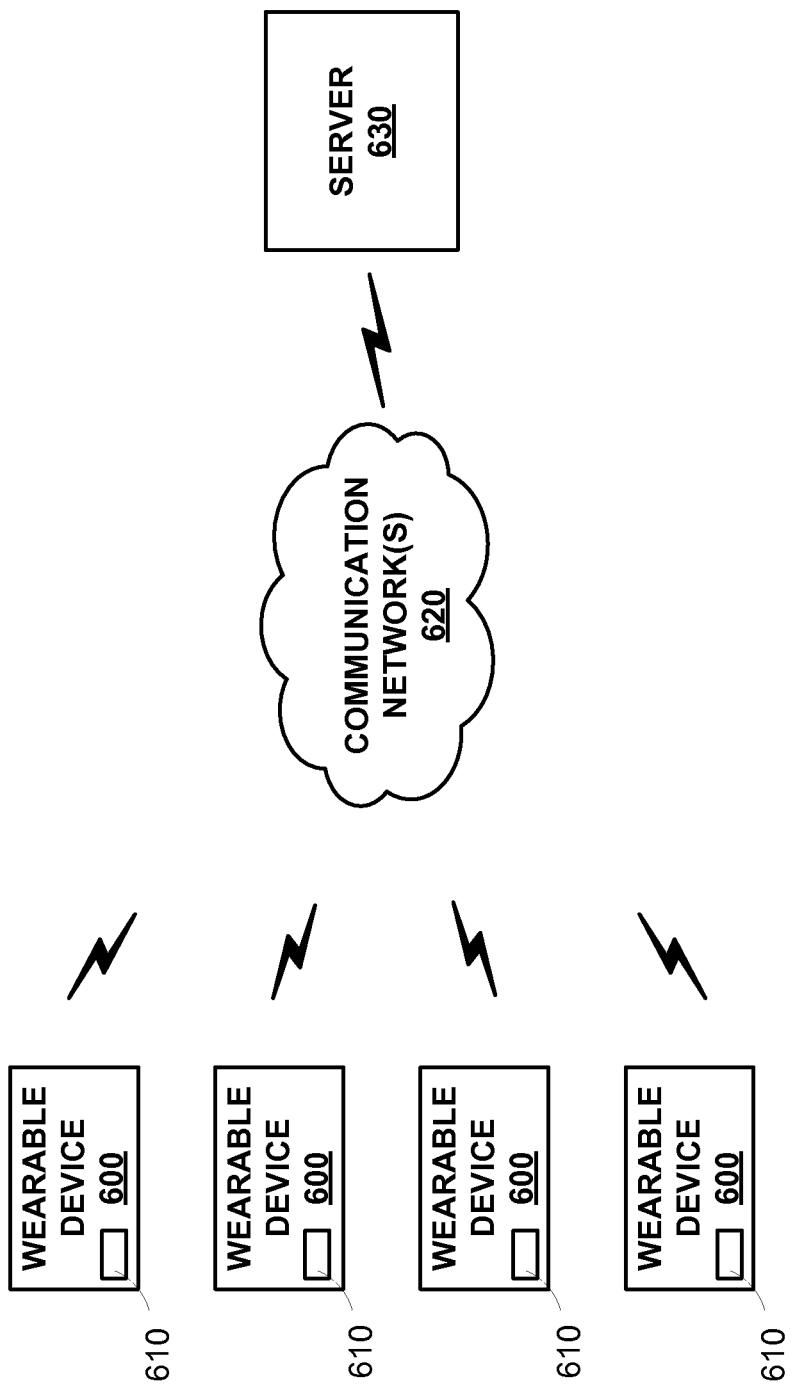

POSITIONING A WEARABLE DEVICE FOR DATA COLLECTION

BACKGROUND

Unless otherwise indicated herein, the materials described in this section are not prior art to the claims in this application and are not admitted to be prior art by inclusion in this section.

Certain medical states or conditions of a human body can be detected using sensors disposed outside of the human body (e.g., disposed against, on, or otherwise proximate an external body surface of the human body). Some medical states or conditions can change slowly, occur rarely, or otherwise indicate that monitoring of the human body over an extended period of time is preferred. A sensor disposed in a wearable device can enable long-term monitoring of a medical state or condition of the body of a wearer while allowing the wearer to perform activities of daily living, to travel, to commute, or to engage in other activities with minimal interruption. Such monitoring by a wearable device could be performed preventatively, e.g., to monitor an otherwise healthy wearer's health state over time to enable early detection of an adverse medical condition, to develop data describing a 'healthy' baseline state of the wearer, or to enable other applications. Medical states or conditions of a human body monitored by such a wearable device can include pulse rate, blood oxygenation, activity level, blood pressure, galvanic skin response, or other information about the body of a wearer.

SUMMARY

Some embodiments of the present disclosure provide a wearable device including: (i) at least two photodetectors, wherein the at least two photodetectors are configured to detect alignment of a target relative to the at least two photodetectors; (ii) a mount configured to mount the at least two photodetectors to an external body surface proximate to the target; and (iii) a controller configured to operate the at least two photodetectors to detect alignment of the target relative to the at least two photodetectors.

Some embodiments of the present disclosure provide a wearable device including: (i) at least two light emitters, wherein the at least two light emitters are configured to illuminate a target; (ii) at least one photodetector, wherein the at least one photodetector is configured to detect alignment of a target relative to the at least one photodetector by detecting light emitted from the target in response to illumination by the at least two light emitters; (iii) a mount configured to mount the at least two light emitters and at least one photodetector to an external body surface proximate to the target; and (iv) a controller configured to operate the at least two light emitters and at least one photodetector to detect alignment of the target relative to the at least one photodetector.

Some embodiments of the present disclosure provide a method that involves mounting a wearable device to an external body surface. The wearable device includes (i) at least one light emitter, (ii) at least one photodetector, (iii) a mount configured to mount the at least one light emitter and at least one photodetector to an external body surface proximate to a target, and (iv) a controller configured to operate the at least one light emitter and at least one two photodetector. The method further involves detecting, by the controller, an alignment of the at least one light emitter and at least one photodetector relative to the target.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6 is a block diagram of an example system that includes a plurality of wearable devices in communication with a server.

DETAILED DESCRIPTION

Figure 1A:
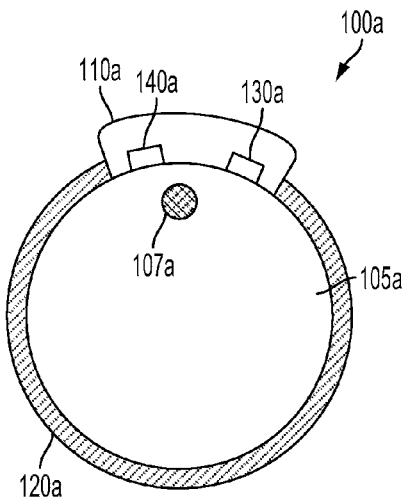
FIG. 1A is a cross-sectional view of an example wearable device while on a human wrist.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of two or more sensors to locate the relative positioning of a target is desired. The environment may be any living or non-living body or a portion thereof, a gel, an emulsion, a fluid conduit, a fluid reservoir, etc. For example, one of skill in the art will recognize that the embodiments disclosed herein may be used to sense a target (e.g., a fluid conduit, pipe, or tube) within a manufactured device or industrial environment or work piece.

I. Overview

A wearable device may be configured to perform a variety of different functions and/or applications. In some examples, a wearable device is configured to measure one or more physiological parameters of the wearer. Measuring one or more physiological parameters of the wearer could include interacting with (e.g., receiving light from, illuminating, detecting a property of) a specific target within the body of the wearer. For example, detecting the concentration of an analyte in the bloodstream of the wearer could include illuminating and detecting light received from a portion of subsurface vasculature (e.g., a vein or artery) beneath the skin of the wearer. Other functions or applications of a wearable device (e.g., delivery of haptic sensations to the wearer, emission of energy to cause a change in one or more analytes in the blood of the wearer) could also be related to a specific target within the body of the wearer. Sensors or other components of a wearable device could be configured to detect the location of such specific targets relative to elements of the wearable device (i.e., to detect the alignment of the target relative to the elements of the wearable device).

The specific target could comprise a variety of elements of the body of a wearer. The target could be a portion of subsurface vasculature (e.g., a vein or artery), a nerve, a muscle, a bone, or some other element of the anatomy of the wearer. In some examples, the target could be an implanted device or object. For example, the target could be an implanted polymer chip configured to have a changing color related to the concentration of an analyte (e.g., glucose) in the environment of the polymer chip. The location of the target relative to the wearable device could include detecting a property of the target that is different from neighboring regions of the body of the wearer. For example, the target could be a vein and the wearable device could detect the color of light received from an external body surface to locate the vein beneath the external body surface. Detected properties of targets could include color, fluorescence intensity, fluorescence absorption spectrum, fluorescence emission spectrum, degree and/or orientation of polarization of reflected, emitted, or scattered light, light absorption spectrum, acoustical absorption spectrum, acoustical reflectivity, radiopacity, RF absorption spectrum, or other properties and/or features of the target.

The location and/or alignment of the target relative to the wearable device could be detected using one or more sensors configured to detect one or more properties of the target. For example, the wearable device could be configured to be mounted to a wrist of the wearer and could include two color sensors configured to detect the alignment of the wearable device relative to a vein in the wrist of the wearer. The color sensors could be separated by a distance related to the width of the vein and in a direction perpendicular to the direction of the vein. As such, the alignment of the vein between the color sensors could be detected by detecting that the output of the color sensors is substantially equal (i.e., that the vein is equidistant to both of the two sensors). In some examples, a plurality of sensors could be provided to detect the alignment of the target relative to the wearable device. The sensors of the plurality of sensors could include a single type of sensor or a plurality of sensor types. The plurality of sensors could include temperature sensors, energy sensors, electromagnetic sensors, light sensors, chemical sensors, acoustical sensors, infrared sensors, ultraviolet sensors, or other types of sensors. For example, the plurality of sensors could include photodetectors (e.g., light detectors, color detectors, polarity detectors, infrared detectors, ultraviolet detectors, cameras). In some examples, one or more of the plurality of sensors could include energy emitters (e.g., light emitters, heaters, acoustical transducers) configured to enable detection of some property of the environment of a sensor by illuminating, heating, or otherwise introducing an energy to the environment of the sensor.

Additionally or alternatively, the location and/or alignment of the target relative to the wearable device could be detected using one or more light emitters configured to emit light to illuminate the target and at least one photodetector configured to detect light emitted from the target in response to the illumination. For example, the wearable device could be configured to be mounted to a wrist of the wearer and could include two or more light emitters configured to emit light into respective regions of the wrist of the wearer (e.g., regions proximate to respective light emitters). Further, light emitted by the light emitters is preferentially reflected, refracted, or otherwise scattered by the target (e.g., by blood in a portion of subsurface vasculature, by a wall of a portion of subsurface vasculature) relative to other elements in the environment of the target (e.g., skin, connective tissue). The light emitters could be operated to emit respective amounts of light over time (e.g., pulses of illumination, alternating between individual light emitters and/or groups thereof between different periods of time) such that the alignment of the target relative to the light emitters and photodetector could be detected by detecting a proximity between the target and individual plight emitters based on a level of light received by the photodetector during respective periods of time corresponding to periods of time during which respective light emitters are emitting light.

The wearable device could include a plurality of sensor and/or light emitters that could be arranged according to an application of the wearable device. For example, the sensors and/or light emitters could be arranged in a linear array. A linear array of sensors and/or light emitters could be especially useful in applications wherein the wearable device is configured to be mounted around a wrist or other protruding anatomy of a wearer. The alignment of such a wearable device with a target (e.g., a vein, nerve, bone, or other anatomical element disposed largely parallel to the direction of the protruding anatomy) could be related to a rotation of the wearable device about the protruding anatomy (e.g., an angle measured about the center of the protruding anatomy between an element of the wearable device and the target in the protruding anatomy) such that a linear array of sensors and/or light emitters arranged along an external surface of the protruding anatomy and perpendicular to the direction of the protruding anatomy could be used to measure the alignment of (e.g., angle between) the wearable device and the target. Other one- and two-dimensional patterns (e.g., rectangular and hexagonal grids) of sensors and/or light emitters are anticipated to enable the detection of the location and/or alignment of a variety of targets according to a variety of applications.

In some examples, the wearable device could detect alignment relative to a target by detecting the location of (and/or alignment relative to) some other alignment feature. In some examples, the alignment feature could have a known and/or specified location or orientation relative to the target, such that detection of the location of the alignment feature could be used to determine the location of the target. For example, the alignment feature could be a tendon in the wrist of a wearer that has a known spatial relationship with a target artery in the wrist. The alignment and/or location of the alignment feature relative to the wearable device could be in some sense easier to detect and/or able to be detected more quickly, more precisely, and/or more accurately by the wearable device than the location of the target relative to the wearable device; as such, determination of the location of the alignment feature could allow a quicker, more precise, more accurate, or in some other way superior determination of the location and/or alignment of the target than a direct determination of the location and/or alignment of the target. In some examples, the alignment feature could be an artificial feature (e.g., a tattoo, a temporary tattoo, a piercing, a label adhered to skin, an implanted marker or other device) having a known location and/or orientation relative to a target. For example, a tattoo comprising a fluorescent dye could be applied to an external body surface above a target (e.g., a nerve). Note that the target could simply be a region of tissue of a wearer having known properties (e.g., a known baseline, a known pattern of innervation, etc.) according to an application. The location of such targets could be detected based on alignment features.

In some examples, detection of the alignment of a target relative to the wearable device could enable the detection of one or more properties of the target and/or of the body of the wearer. For example, a sensor of the wearable device could be configured to detect the concentration of an analyte in the blood when the sensor is aligned with a portion of vasculature of the wearer. Detection of the alignment of the portion of vasculature with the wearable device (i.e., with the sensor) could be used to operate the sensor to detect the concentration of the analyte in the blood in the portion of vasculature. Additionally or alternatively, the sensors employed to detect the alignment of the target could additionally be configured to detect one or more properties of the target and/or of the body of the wearer. The presence of two or more such sensors could enable detection of the one or more properties across a wider variety of relative alignments of the target with the wearable device. In some examples, detection of the alignment of a target relative to the wearable device could enable the modification of some element of the body of the wearer by the wearable device. For example, an energy emitter (e.g., a light source, an RF emitter, an acoustic transducer) of the wearable device could be configured to modify (e.g., heat, denature, destroy, cause a change in state of) an analyte in the blood when the energy emitter is aligned with a portion of vasculature of the wearer. Detection of the alignment of the portion of vasculature with the wearable device (i.e., with the energy emitter) could be used to operate the energy emitter to modify the analyte in the blood in the portion of vasculature. Other applications of detection of the location and/or alignment of a target relative to a wearable device are anticipated.

Detection of the alignment and/or location of a target relative to the wearable device could be used to effect a change in the alignment between the target and the wearable device. In some examples, the wearable device could be configured to indicate the level, direction, angle, or some other property of the detected alignment (e.g., by providing a tone, a vibration, a visual indication) such that the wearer could adjust the wearable device to align the wearable device with the target (e.g., by rotating the wearable device about a wrist to which the wearable device is mounted). In some examples, the wearable device could include an actuator (e.g., a motor, a solenoid) and the actuator could be operated to adjust the alignment of an element or elements (e.g., a sensor, an energy emitter) of the wearable device with the target. Adjustment of the alignment of the wearable device could be indicated/effected periodically or in response to some condition (e.g., a determination that the alignment between the wearable device and the target had decreased below some threshold level).

In some examples, the wearable device may include a user interface that is configured to provide user-discernible indications (e.g., visual, audible, and/or tactile indications) of information sensed by sensors of the wearable device, progress or other information related to a function of the device, or other information. In some examples, the user interface could additionally provide a means for one or more settings of the wearable device (e.g., a sampling rate, a user information privacy setting, a user's credentials to access a service) to be specified by a wearer according to the wearer's preferences. In some examples, the wearable device may include a wireless communication interface that can transmit/receive data to/from an external device, for example, using Bluetooth, ZigBee, WiFi, and/or some other wireless communication protocol. The data transmitted by the wireless communication interface may include data indicative of one or more physiological parameters measured by the device, the alignment of a target relative to the device, a blood oxygenation level, or the concentration of an analyte in the blood of the wearer. The wireless communications interface could additionally or alternatively be configured to receive data from an external system (e.g., parameters relating to the operation of an energy emitter configured to emit energy into blood of the wearer to effect a change in some analyte in the blood).

II. Example Wearable Devices

Wearable devices as described herein can be configured to be mounted to an external body surface of a wearer and to enable a variety of applications and functions including the detection of alignment between a target on or within the body of the wearer and one or more components of the wearable devices. Two or more sensors (e.g., photodetectors) and/or two or more light emitters could be used to detect alignment of a target on or within the body of the wearer when the wearable device is mounted to the external body surface. Alignment could include the target having a relative location and/or orientation relative to elements of the wearable device (e.g., the at least two sensors, the at least two light emitters) in one or more dimensions. Such wearable devices could enable a variety of applications, including measuring physiological information about a wearer, indicating such measured physiological information or other information to the wearer (e.g., using a vibrator, a screen, a beeper), or other functions. The wearable device could be operated relative to a target alignment detected using the at least two sensors.

The two or more sensors and/or two or more light emitters being used to detect the alignment of a target could include detecting a location, orientation, or some other information about the configuration of the target relative to the location, orientation, and/or configuration of the two or more sensors, two or more light emitters, and/or other elements of a wearable device. In some examples, detecting alignment of the target could include detecting and/or generating a continuous variable related to the alignment of the target. For example, the two or more sensors and/or two or more light emitters could be configured to detect a distance and/or direction between the location of the target and the location of an element of the wearable device.

In some examples, detecting alignment of the target could include determining categorical and/or qualitative information related to the alignment of the target. For example, the two or more sensors and/or two or more light emitters could be configured to generate information to determine a binary variable related to whether the target is "aligned" (e.g., location within and/or passing through a specified region relative to the wearable device). Alignment of a target could include the target being within and/or partially occupying a specified region relative to the two or more sensors, two or more light emitters, and/or other elements of the wearable device. For example, alignment could include the target occupying and/or passing through a region directly below one of the two or more sensors and/or two or more light emitters, a region midway between two sensors or two light emitters, or some other specified region or regions. Alignment of a target could include the target being within and/or partially occupying one of more than one specified region. For example, alignment could include the target occupying and/or passing through a region directly below any particular sensor and/or light emitter in an array of two or more sensors and/or two or more light emitters.

FIG. 1A is a partial cross-sectional view through a human wrist 105a illustrating an example wearable device 100a when mounted to the human wrist 105a. The wearable device 100a includes a housing 110a (e.g., a water-resistant and/or water-proof housing) configured to contain electronic components and to be mounted to an external body surface of a wearer by a mount 120a. The mount 120a can be a band configured to enclose the wrist 105a and to position first 130b and second 140a sensors in the housing 110a proximate to a target 107a (i.e., a portion of subsurface vasculature) in the wrist 105a. The wearable device 100a includes additional elements that are not shown, e.g., electronics configured to operate the first 130a and second 140a sensors and to enable applications and/or functions of the wearable device 100a, a rechargeable battery configured to power the wearable device 100a, or other components. Components of the wearable device 100a could be disposed on or within the housing 110a, the mount 120a, or some other elements of the wearable device 100a (not shown); e.g., a second housing.

The housing 110a could be configured to be water-resistant and/or water-proof. That is, the housing 110a could be configured to include sealants, adhesives, gaskets, welds, press-fitted seams, and/or other joints such that the housing 110a was resistant to water entering an internal volume or volumes of the housing 110a when the housing 110a is exposed to water. The housing 110a could further be water-proof, i.e., resistant to water entering an internal volume or volumes of the housing 110a when the housing 110a is submerged in water. For example, the housing 110a could be water-proof to a depth of 1 meter, i.e., configured to resist water entering an internal volume or volumes of the housing 110a when the housing 110a is submerged to a depth of 1 meter. Further, the interface between the housing 110a and other elements of the wearable device 100a (e.g., elements of a sensor, buttons, user interface elements, electrical contacts, sensors 130a, 140a) protruding from, embedded in the surface of, or otherwise interrupting the material of the housing 110a could be configured such that the combination of the housing 110a and the other elements of the wearable device 100a is water-resistant and/or water-proof.

The sensors 130a, 140a could include one or more photodetectors (e.g., light sensors, IR sensors, UV sensors), electric field sensors, magnetic field sensors, electromagnetic energy sensors, temperature sensors, electric current sensors, electric potential sensor, acoustical sensors, force transducers, or some other sensors or combination(s) of sensors. The sensors 130a, 140a could include one or more light emitters, IR emitters, electromagnetic energy emitters, heaters, vibrators, acoustical energy emitters, force transducers, or some other energy emitters. One or both of the sensors 130a, 140a could be configured to operate in direct contact with an external body surface of the wearer (e.g., configured to include a heat- or electricity-conducting probe or other element in physical contact with the skin of the wearer to facilitate detection of one or more properties of the body of the wearer). Additionally or alternatively, one or both of the sensors 130a, 140a could be configured to indirectly (i.e., without directly contacting an external body surface of the wearer) detect information about the target 107a or some other element or elements of the wearer's body (e.g., to detect electromagnetic, optical, acoustical, or other fields and/or energies emitted, reflected, scattered and/or generated by elements of the wearer's body and received by the sensors 130a, 140a).

The sensors 130a, 140a could interact with and/or detect one or more properties of specific elements or components of the body of the wearer (e.g., the target 107a). In some examples, one or both of the sensors 130a, 140a could act to illuminate or otherwise direct energy toward elements in the body of the wearer (e.g., the target 107a) and could detect a light or other energy emitted by, reflected by, scattered by, or otherwise received from the elements in response to the illumination and/or direction of energy toward the elements. For example, one or both of the sensors 130a, 140a could be configured to illuminate a fluorophore, chromophore, or other optic chemical, moiety, analyte, or other element of the body of the wearer and to detect light emitted, scattered, reflected, or otherwise received from the element of the body of the wearer in response to the illumination. One or more properties of the illumination and/or of the detected light could be used to determine one or more properties of the body of the wearer. For example, a color of light received by a sensor could be used to determine whether the target 107a (a portion of subsurface vasculature) is in a specified direction (i.e., a direction of light sensitivity of the sensor) by comparing the color of the received light to an expected color of the target 107a (e.g., a blue color of a vein). In another example, a sensor could be configured to emit a pulse of acoustic energy and to detect a time delay of acoustic energy reflected by the target 107a; the detected time delay could be related to a distance between the sensor and the target 107a.

In some examples, the body of the wearer (e.g., the target 107a, i.e., subsurface vasculature) could include artificial or other contrast agents (e.g., fluorophores, fluorescent nanodiamonds, chromophores, acoustic particles, magnetic particles) functionalized or otherwise configured to enable the detection of alignment of the target 107a and/or of one or more properties of the body of the wearer using sensors (e.g., 130a, 140a) of the wearable device 100a. For example, a contrast agent including a fluorophore could be configured to selectively bind to an analyte of interest in the blood of the wearer, and a sensor (e.g., 130a, 140a) could be operated to determine to presence, location, binding state, or other properties of the contrast agent in the blood. The determined one or more properties of the contrast agent could be used to determine an alignment of the target 107a relative to the sensor and/or other component(s) of the wearable device 100a. Other contrast agents, properties of the body of the wearer, and configurations and method of operation of the wearable device 100a are anticipated.

As illustrated in FIG. 1A, the target 107a is located beneath the housing 110a, at a location between the first 130a and second 140a sensors. In some embodiments, the first 130a and second 140a sensors could be configured to determine the location of the target 107a relative to the sensors 130a, 140a, the housing 110a, or some other element(s) of the wearable device 100a. That is, detecting alignment of the target 107a could include operating the sensors 130a, 140a, to detect the location, orientation, or some other information about the disposition of the target 107a. In some embodiments, the illustrated location of the target 107a relative to the sensors 130a, 140a, housing 110a, and/or other components of the wearable device 100a could be one of one or more specified locations, such that the target 107a is aligned relative to element(s) of the wearable device 100a. Thus, the sensors 130a, 140a could be operated as described above to detect the location, orientation, or some other information about the target 107a and a determination that the target 107a is aligned could be made based on such detected information. Additionally or alternatively, the sensors 130a, 140a could be configured to detect some categorical and/or qualitative information about the alignment of the target 107a. For example, the sensors 130a, 140a could be configured to detect that the alignment of the target 107a corresponds to one of a discrete set of states, e.g., 'aligned,' 'nearly aligned,' 'not aligned,' 'not aligned in the direction of the first sensor 130a,' 'not aligned in the direction of the second sensor 140a,' etc. That is, in some examples the disposition of the target 107a relative to component(s) of the wearable device 100a could be such that the target 107a is not aligned.

Figure 1B:
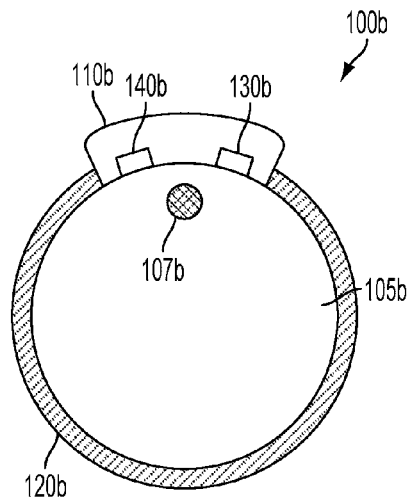
FIG. 1B is a cross-sectional view of an example wearable device while on a human wrist and while two sensors of the example wearable device are aligned with a target in the wrist.

FIG. 1B is a partial cross-sectional view through a human wrist 105b illustrating an example wearable device 100b when mounted to the human wrist 105b. The wearable device 100b could be configured similarly to the wearable device 100a of FIG. 1A, and includes a housing 110b (e.g., a water-resistant and/or water-proof housing) configured to contain electronic components and to be mounted to an external body surface of a wearer by a mount 120b. The mount 120b can be a band configured to enclose the wrist 105b and to position first 140b and second 140b sensors in the housing 110b proximate to a target 107b (i.e., a portion of subsurface vasculature) in the wrist 105b.

As illustrated in FIG. 1B, the target 107b is located beneath the housing 110b, at a location midway between the first 130b and second 140b sensors. In some embodiments, the first 130b and second 140b sensors could be configured to determine the location of the target 107b relative to the sensors 130b, 140b, the housing 110b, or some other element(s) of the wearable device 100a. That is, detecting alignment of the target 107b could include operating the sensors 130b, 140b, to detect the location, orientation, or some other information about the disposition of the target 107b. In some embodiments, the illustrated location of the target 107b relative to the sensors 130b, 140b, housing 110b, and/or other components of the wearable device 100b could be one of one or more specified locations, such that the target 107b is aligned relative to element(s) of the wearable device 100b. Thus, the sensors 130a, 140a could be operated as described above to detect the location, orientation, or some other information about the target 107b and a determination that the target 107b is aligned could be made based on such detected information. Additionally or alternatively, the sensors 130b, 140b could be configured to detect some categorical and/or qualitative information about the alignment of the target 107b. For example, the sensors 130b, 140b could be configured to detect that the alignment of the target 107b corresponds to one of a discrete set of states, e.g., 'aligned,' 'nearly aligned,' 'not aligned,' 'not aligned in the direction of the first sensor 130b,' 'not aligned in the direction of the second sensor 140b,' etc. For example, the sensors 130b, 140b could determine that the target 107b is aligned based on a property detected by the sensors 130b, 140b (e.g., a reflected light intensity, an echo signal latency) being substantially equal.

Figure 1C:
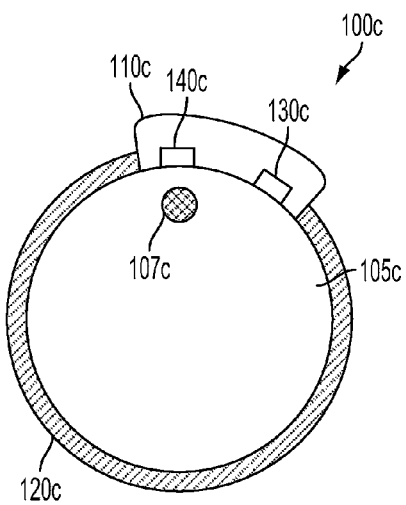
FIG. 1C is a cross-sectional view of an example wearable device while on a human wrist and while a particular sensor of the example wearable device is aligned with a target in the wrist.

FIG. 1C is a partial cross-sectional view through a human wrist 105c illustrating an example wearable device 100c when mounted to the human wrist 105c. The wearable device 100c could be configured similarly to the wearable devices 100a, 100b of FIGS. 1A and 1B, and includes a housing 110c (e.g., a water-resistant and/or water-proof housing) configured to contain electronic components and to be mounted to an external body surface of a wearer by a mount 120c. The mount 120c can be a band configured to enclose the wrist 105c and to position first 140c and second 140c sensors in the housing 110c proximate to a target 107c (i.e., a portion of subsurface vasculature) in the wrist 105c.

As illustrated in FIG. 1C, the target 107c is located beneath the housing 110c, at a location beneath the second 140c sensor. In some embodiments, the first 130c and second 140c sensors could be configured to determine the location of the target 107c relative to the sensors 130c, 140c, the housing 110c, or some other element(s) of the wearable device 100c. That is, detecting alignment of the target 107c could include operating the sensors 130c, 140c, to detect the location, orientation, or some other information about the disposition of the target 107c. In some embodiments, the illustrated location of the target 107c relative to the sensors 130c, 140c, housing 110c, and/or other components of the wearable device 100c could be one of one or more specified locations, such that the target 107c is aligned relative to element(s) of the wearable device 100c. Additionally or alternatively, the target 107c being located beneath the first sensor 130c could be one of one or more specified alignment locations. Thus, the sensors 130c, 140c could be operated as described above to detect the location, orientation, or some other information about the target 107c and a determination that the target 107c is aligned could be made based on such detected information. Additionally or alternatively, the sensors 130c, 140c could be configured to detect some categorical and/or qualitative information about the alignment of the target 107c. For example, the sensors 130c, 140c could be configured to detect that the alignment of the target 107c corresponds to one of a discrete set of states, e.g., 'aligned,' 'aligned with the first sensor 130c,' 'aligned with the second sensor 140c,' 'nearly aligned,' 'not aligned,' 'not aligned in an upward direction,' 'not aligned in a downward direction,' etc. In some examples, the sensors 130c, 140c could determine that the target 107c is aligned based on a property detected by the sensors 130b, 140c (e.g., a reflected light intensity, an echo signal latency) being substantially equal to some minimal or maximal value.

In some examples, one or more sensors of a wearable device as described herein could be configured to detect some physiological or other property of the wearer in addition to detecting the alignment of a target on or within the body of the wearer. For example, the second sensor 140c of the wearable device 100c illustrated in FIG. 1C could be configured to detect a physiological or other property of the wearer and/or of the target 107c (e.g., a blood flow rate, a pulse rate, a blood oxygenation, a blood temperature, a concentration of an analyte in blood) when the second sensor 140c is aligned with (e.g., disposed above) the target 107c. Further operation of the second sensor 140c to detect the physiological property could be performed in response to a determination (e.g., using the first 130c and/or second 140c sensors) that the target 107c is aligned with the second sensor 140c. Additionally or alternatively, operation of the second sensor 140c to detect the physiological property could be related to the detected alignment (e.g., detected using the first 130c and second 140c sensors). For example, a mapping or other calculation performed to determine a value of a detected physiological property based on a measurement generated by the second sensor 140c could be based on a determined and/or detected alignment of the target 107c; e.g., an amplitude of a generated measurement could be normalized based on a detected alignment of the target 107c to correct for effects of proximity between the target 107c and the second sensor 140c on measurements generated by the second sensor 140c.

Additionally or alternatively, a wearable device could include two or more sensors configured to detect alignment of a target, and one or more further sensors configured to detect a physiological or other property (e.g., a blood flow rate, a pulse rate, a blood oxygenation, a blood temperature, a concentration of an analyte in blood) of the wearer and/or of the target. The further sensor(s) could be configured to detect the property of the wearer and/or target when the target has a specified disposition (e.g., location, orientation) relative to the further sensor (i.e., when the target is aligned with the further sensor). The operation of the further sensor to detect the property of the wearer and/or target could be performed in response to a determination (e.g., using the two or more sensors) that the target is aligned with the further sensor. Additionally or alternatively, operation of the further sensor to detect the property of the wearer and/or target could be related to the detected alignment. For example, a mapping or other calculation performed to determine a value of a detected property based on a measurement generated by the further sensor could be based on a determined and/or detected alignment of the target; e.g., an amplitude of a generated measurement could be normalized based on a detected alignment of the target to correct for effects of proximity between the target and the further sensor on measurements generated by the further sensor.

Figure 1D:
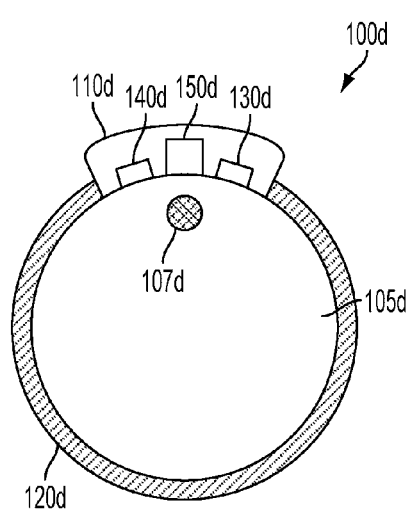
FIG. 1D is a cross-sectional view of an example wearable device while on a human wrist and while a particular sensor of the example wearable device is aligned with a target in the wrist.

FIG. 1D illustrates such a wearable device 100d. FIG. 1D is a partial cross-sectional view through a human wrist 105d illustrating an example wearable device 100d when mounted to the human wrist 105d. The wearable device 100d could be configured similarly to the wearable devices 100a, 100b, 100c of FIGS. 1A, 1B, and 1C, and includes a housing 110d (e.g., a water-resistant and/or water-proof housing) configured to contain electronic components and to be mounted to an external body surface of a wearer by a mount 120d. The mount 120d can be a band configured to enclose the wrist 105d and to position first 140d and second 140d sensors in the housing 110d proximate to a target 107d (i.e., a portion of subsurface vasculature) in the wrist 105d. The wearable device 100d further includes a further sensor 150d configured to detect one or more physiological properties of the wearer (e.g., of the target 107d) when the target 107d is aligned with the wearable device 100d (i.e., aligned with the further sensor 150d).

As illustrated in FIG. 1D, the target 107d is located beneath the housing 110d, at a location beneath the further sensor 150d. In some embodiments, the first 130d and second 140d sensors could be configured to determine the location of the target 107d relative to the sensors 130d, 140d, the housing 110d, the further sensor 150d, or some other element(s) of the wearable device 100d. That is, detecting alignment of the target 107d could include operating the sensors 130d, 140d, to detect the location, orientation, or some other information about the disposition of the target 107d. The further sensor 150d could also be configured to detect, alone or in concert with the other sensors 130d, 140d, the alignment of the target 107d. Thus, the sensors 130d, 140d could be operated as described above to detect the location, orientation, or some other information about the target 107d and a determination that the target 107d is aligned could be made based on such detected information. Additionally or alternatively, the sensors 130d, 140d could be configured to detect some categorical and/or qualitative information about the alignment of the target 107d. For example, the sensors 130d, 140d could be configured to detect that the alignment of the target 107d corresponds to one of a discrete set of states, e.g., 'aligned,' 'nearly aligned,' 'not aligned,' 'not aligned in a direction toward the first sensor 130d,' 'not aligned in a direction toward the second sensor 140d,' etc. In some examples, the sensors 130d, 140d could determine that the target 107d is aligned based on a property detected by the sensors 130d, 140d (e.g., a reflected light intensity, an echo signal latency) being substantially equal.

Note that the further sensor 150d could include an energy emitter configured to emit some energy (e.g., light, infrared, ultraviolet, acoustic, ultrasonic, electromagnetic, thermal, etc.). The energy could be emitted to enable detection of some property of the wearer and/or a target (e.g., 107d) by active detection (i.e., illuminating or otherwise exposing the target to energy such that a change in the target (e.g., a fluorescence, a temperature change, a scattering of energy) related to the property can be detected). Alignment of a target with the further sensor 150d could include alignment of the target with the energy emitter. The further sensor 150d could include other elements, including but not limited to magnets, filters, polarizers, magnetic shimming and/or shielding materials, and diffraction gratings.

Additionally or alternatively, the further sensor 150d illustrated in FIG. 1D could include some other element, component, or device. In some examples, the wearable device 100d could include an energy emitter configured to emit some energy (e.g., visible light, infrared light, ultraviolet light, heat, acoustical pulses) in order to effect some change in the body of the wearer and/or components thereof (e.g., to denature, destroy, or otherwise alter some analyte in the subsurface vasculature of the wearer that has a negative health effect on the wearer, e.g., a cancer cell). In some examples, the wearable device 100d could include a high-strength magnet configured to attract magnetic particles in a lumen of subsurface vasculature proximate to the high-strength magnet, and two or more sensors of the wearable device could be configured to detect alignment of the subsurface vasculature (i.e., the target) with the high-strength magnet such that magnetic fields emitted by the high-strength magnet can act to attract, collect, or otherwise exert magnetic forces on the magnetic particles. Other configurations, operations, and applications of wearable devices, and alignments with component(s) of such wearable devices to enable or otherwise affect such operations and/or applications, are anticipated.

Figure 1E:
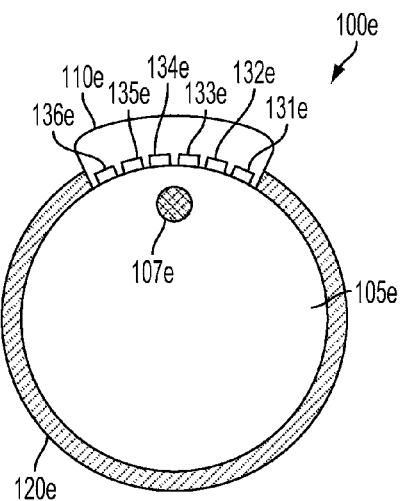
FIG. 1E is side partial cross-sectional view of an example wearable device while on a human wrist.

A wearable device could include a plurality of sensors configured in a variety of ways to enable detection of alignment of a target relative to the plurality of sensors and/or other component(s) of the wearable device. FIG. 1E illustrates such a wearable device 100e. FIG. 1E is a partial cross-sectional view through a human wrist 105e illustrating an example wearable device 100e when mounted to the human wrist 105e. The wearable device 100e could be configured similarly to the wearable devices 100a, 100b, 100c of FIGS. 1A, 1B, and 1C, and includes a housing 110e (e.g., a water-resistant and/or water-proof housing) configured to contain electronic components and to be mounted to an external body surface of a wearer by a mount 120e. The mount 120e can be a band configured to enclose the wrist 105e and to position a plurality of sensors 131e, 132e, 133e, 134e, 135e, 136e in the housing 110e proximate to a target 107e (i.e., a portion of subsurface vasculature) in the wrist 105e.

As illustrated in FIG. 1E, the target 107e is located beneath the housing 110e, at a location proximate to the sensors 131e, 132e, 133e, 134e, 135e, 136e. In some embodiments, the sensors 131e, 132e, 133e, 134e, 135e, 136e could be configured to determine the location of the target 107e relative to the sensors 131e, 132e, 133e, 134e, 135e, 136e, the housing 110e, or some other element(s) of the wearable device 100e. That is, detecting alignment of the target 107e could include operating the sensors 131e, 132e, 133e, 134e, 135e, 136e to detect the location, orientation, or some other information about the disposition of the target 107e. In some embodiments, the illustrated location of the target 107e relative to the sensors 131e, 132e, 133e, 134e, 135e, 136e, housing 110e, and/or other components of the wearable device 100e could be one of one or more specified locations, such that the target 107e is aligned relative to element(s) of the wearable device 100e. Thus, the sensors 131e, 132e, 133e, 134e, 135e, 136e could be operated as described above to detect the location, orientation, or some other information about the target 107e and a determination that the target 107e is aligned could be made based on such detected information. Additionally or alternatively, the sensors 131e, 132e, 133e, 134e, 135e, 136e could be configured to detect some categorical and/or qualitative information about the alignment of the target 107e. For example, the sensors 131e, 132e, 133e, 134e, 135e, 136e could be configured to detect that the alignment of the target 107e corresponds to one of a discrete set of states, e.g., 'aligned,' 'nearly aligned,' 'not aligned,' 'aligned with a first sensor 131e,' 'aligned with a second sensor 132e,' 'not aligned between a first set of two sensors 131e, 132e,' 'not aligned between a second pair of sensors 132e, 133e,' 'not aligned between a third pair of sensors 133e, 134e,' etc. That is, in some examples the disposition of the target 107e relative to component(s) of the wearable device 100e could be such that the target 107e is not aligned.

Figure 1F:
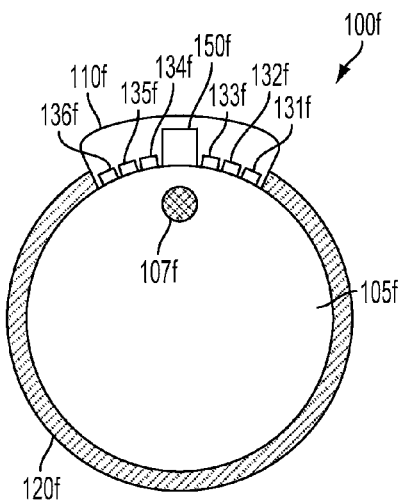
FIG. 1F is a cross-sectional view of an example wearable device while on a human wrist and while a particular sensor of the example wearable device is aligned with a target in the wrist.

FIG. 1F is a partial cross-sectional view through a human wrist 105f illustrating an example wearable device 100f when mounted to the human wrist 105f. The wearable device 100f could be configured similarly to the wearable devices 100a, 100b, 100c, 100d, 100e of FIGS. 1A, 1B, 1C, 1D, and 1E, and includes a housing 110f (e.g., a water-resistant and/or water-proof housing) configured to contain electronic components and to be mounted to an external body surface of a wearer by a mount 120f. The mount 120f can be a band configured to enclose the wrist 105f and to position a plurality of sensors 131f, 132f, 133f, 134f, 135f, 136f in the housing 110f proximate to a target 107f (i.e., a portion of subsurface vasculature) in the wrist 105f. The wearable device 100f further includes a further sensor 150f configured to detect one or more physiological properties of the wearer (e.g., of the target 107f) when the target 107f is aligned with the wearable device 100f (i.e., aligned with the further sensor 150f).

As illustrated in FIG. 1F, the target 107f is located beneath the housing 110f, at a location beneath the further sensor 150d. In some embodiments, the sensors 131f, 132f, 133f, 134f, 135f, 136f could be configured to determine the location of the target 107f relative to the sensors 131f, 132f, 133f, 134f, 135f, 136f, the housing 110f, the further sensor 150f, or some other element(s) of the wearable device 100f. That is, detecting alignment of the target 107f could include operating the sensors 131f, 132f, 133f, 134f, 135f, 136f to detect the location, orientation, or some other information about the disposition of the target 107f. The further sensor 150f could also be configured to detect, alone or in concert with the other sensors 131f, 132f, 133f, 134f, 135f, 136f, the alignment of the target 107f. Thus, the sensors 131f, 132f, 133f, 134f, 135f, 136f could be operated as described above to detect the location, orientation, or some other information about the target 107f and a determination that the target 107f is aligned could be made based on such detected information. Additionally or alternatively, the sensors 131f, 132f, 133f, 134f, 135f, 136f could be configured to detect some categorical and/or qualitative information about the alignment of the target 107f. For example, the sensors 131f, 132f, 133f, 134f, 135f, 136f could be configured to detect that the alignment of the target 107f corresponds to one of a discrete set of states, e.g., 'aligned,' 'nearly aligned,' 'not aligned,' 'aligned with the further sensor 150f,' 'aligned with a first sensor 131f,' 'aligned with a second sensor 132f,' 'not aligned between a first set of two sensors 131f, 132f,' 'not aligned between a second pair of sensors 132f, 133f,' 'not aligned between a third pair of sensors 134f, 135f,' etc. That is, in some examples the disposition of the target 107f relative to component(s) of the wearable device 100f (e.g., the further sensor 150f) could be such that the target 107f is not aligned.

Note that the further sensor 150f could include an energy emitter configured to emit some energy (e.g., light, infrared, ultraviolet, acoustic, ultrasonic, electromagnetic, thermal, etc.). The energy could be emitted to enable detection of some property of the wearer and/or a target (e.g., 107f) by active detection (i.e., illuminating or otherwise exposing the target to energy such that a change in the target (e.g., a fluorescence, a temperature change, a scattering of energy) related to the property can be detected). Alignment of a target with the further sensor 150f could include alignment of the target with the energy emitter. The further sensor 150f could include other elements, including but not limited to magnets, filters, polarizers, magnetic shimming and/or shielding materials, and diffraction gratings.

Additionally or alternatively, the further sensor 150f illustrated in FIG. 1F could include some other element, component, or device. In some examples, the wearable device 100f could include an energy emitter configured to emit some energy (e.g., visible light, infrared light, ultraviolet light, heat, acoustical pulses) in order to effect some change in the body of the wearer and/or components thereof (e.g., to denature, destroy, or otherwise alter some analyte in the subsurface vasculature of the wearer that has a negative health effect on the wearer, e.g., a cancer cell). In some examples, the wearable device 100f could include a high-strength magnet configured to attract magnetic particles in a lumen of subsurface vasculature proximate to the high-strength magnet, and two or more sensors of the wearable device could be configured to detect alignment of the subsurface vasculature (i.e., the target) with the high-strength magnet such that magnetic fields emitted by the high-strength magnet can act to attract, collect, or otherwise exert magnetic forces on the magnetic particles. Other configurations, operations, and applications of wearable devices, and alignments with component(s) of such wearable devices to enable or otherwise affect such operations and/or applications, are anticipated.

Figure 1G:
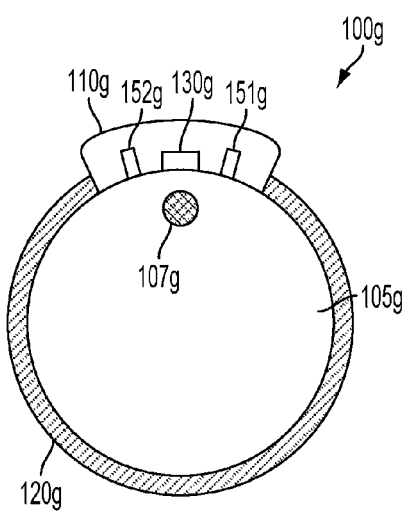
FIG. 1G is a cross-sectional view of an example wearable device while on a human wrist and while a sensor of the example wearable device is aligned with a target in the wrist.

FIG. 1G is a partial cross-sectional view through a human wrist 105g illustrating an example wearable device 100g when mounted to the human wrist 105g. The wearable device 100g could be configured similarly to the wearable devices 100a, 100b, 100c, 100d, 100e, 100f of FIGS. 1A, 1B, 1C, 1D, 1E, and 1F and includes a housing 110g (e.g., a water-resistant and/or water-proof housing) configured to contain electronic components and to be mounted to an external body surface of a wearer by a mount 120g. The mount 120g can be a band configured to enclose the wrist 105g and to position a photodetector 130g and first 151g and second 152g light emitters in the housing 110g proximate to a target 107g (i.e., a portion of subsurface vasculature) in the wrist 105g.

The light emitters 151g, 152g could include a variety of light-emitting components (e.g., LEDS, lasers, electroluminescent panels or wire, IR emitters, UV emitters), refracting elements (e.g., lenses, dichroic elements), reflecting elements (e.g., flat or curved mirrors), diffracting elements (e.g., gratings), polarizers, half or quarter wave plates, filters, apertures, liquid crystal elements (e.g., electronically actuated blinds, gratings, and/or apertures) or some other optical and/or light-emitted elements or combination(s) thereof. The light emitters 151g, 152g could be configured to emit illumination having one or more specified properties (e.g., a wavelength, a spectral profile, a degree and/or direction of polarization). Such specified properties of the light emitted by the light emitters 151g, 152g could be specified such that the light emitted by the light emitters 151g, 152g is preferentially reflected, refracted, or otherwise scattered by the target (e.g., by blood in a portion of subsurface vasculature) relative to other elements in the environment of the target (e.g., skin, connective tissue). The light emitters 151g, 152g could be configured to illuminate specified region(s) of the environment of the wearable device 100g (e.g., regions proximate to respective emitters of the light emitters 151g, 152g). Such illuminated regions could be disjoint or otherwise distinct or could be wholly or partially overlapping.

The photodetector 130g could include one or more light sensitive elements (e.g., light sensors, IR sensors, UV sensors, photodiodes, phototransistors, photoresistors). The photodetector 130g could additionally include one or more light emitters, IR emitters, electromagnetic energy emitters, heaters, vibrators, acoustical energy emitters, force transducers, or some other energy emitters. In addition to detecting alignment of the target 107g in conjunction with the light emitters 151g, 152g, the photodetector 130g could be configured to detect one or more properties (e.g., an oxygen saturation, an analyte presense or concentration) of the target 107g. Such detection could be related to illumination of the target 107g by the light emitters 151g, 152g and/or by emission of energy (e.g., IR, UV, or visible light, heat, electromagnetic radiation, acoustic energy) by an energy emitter of the photodetector 130g.

Additionally or alternatively, the photodetector 130g could be configured to interact with and/or detect one or more properties of specific elements or components of the body of the wearer (e.g., the target 107g). In some examples, the photodetector 130g and/or light emitters 152g, 152g could act to illuminate or otherwise direct energy toward elements in the body of the wearer (e.g., the target 107g) and could detect a light or other energy emitted by, reflected by, scattered by, or otherwise received from the elements in response to the illumination and/or direction of energy toward the elements. For example, one or both of the light emitters 151g, 152g and/or a light emitter of the photodetector 130g could be configured to illuminate a fluorophore, chromophore, or other optic chemical, moiety, analyte, or other element of the body of the wearer and the photodetector 130g could detect light emitted, scattered, reflected, or otherwise received from the element of the body of the wearer in response to the illumination. One or more properties of the illumination and/or of the detected light could be used to determine one or more properties of the body of the wearer. For example, an intensity of light received by the photodetector 130g when the first light emitter 151g is emitting light could be used to determine whether the target 107g (a portion of subsurface vasculature) is in a specified direction (i.e., a direction of light emitted by the first light emitter 151g).

As illustrated in FIG. 1G, the target 107g is located beneath the housing 110g, at a location beneath the photodetector 130g. In some embodiments, the photodetector 130g and first 151g and second 152g light emitters could be configured to determine the location of the target 107g relative to the light emitters 151g, 151g, the housing 110g, the photodetector 130g, or some other element(s) of the wearable device 100g. That is, detecting alignment of the target 107g could include operating the light emitters 151g, 152g and photodetector 130g to detect the location, orientation, or some other information about the disposition of the target 107g. Thus, the light emitters 151g, 152g and photodetector 130g could be operated as described above to detect the location, orientation, or some other information about the target 107g and a determination that the target 107g is aligned could be made based on such detected information. Additionally or alternatively, the light emitters 151g, 152g and photodetector 130g could be configured to detect some categorical and/or qualitative information about the alignment of the target 107g. For example, the light emitters 151g, 152g and photodetector 130g could be configured to detect that the alignment of the target 107g corresponds to one of a discrete set of states, e.g., 'aligned,' 'nearly aligned,' 'not aligned,' 'not aligned in a direction toward the first light emitter 151g,' 'aligned in a direction toward the second light emitter 152g,' etc. In some examples, the light emitters 151g, 152g and photodetector 130g could determine that the target 107g is aligned based on a property detected by the photodetector 130g during periods of operation of the light emitters 151g, 152g (e.g., a reflected light intensity) being substantially equal.

Note that the photodetector 130g could include an energy emitter configured to emit some energy (e.g., light, infrared, ultraviolet, acoustic, ultrasonic, electromagnetic, thermal, etc.). The energy could be emitted to enable detection of some property of the wearer and/or a target (e.g., 107g) by active detection (i.e., illuminating or otherwise exposing the target to energy such that a change in the target (e.g., a fluorescence, a temperature change, a scattering of energy) related to the property can be detected). Alignment of a target with the photodetector 130g could include alignment of the target with the energy emitter of the photodetector 130g. The photodetector 130g could include other elements, including but not limited to magnets, filters, polarizers, magnetic shimming and/or shielding materials, and diffraction gratings.

Additionally or alternatively, the photodetector 130g illustrated in FIG. 1F could include some other element, component, or device. In some examples, the wearable device 100f could include an energy emitter configured to emit some energy (e.g., visible light, infrared light, ultraviolet light, heat, acoustical pulses) in order to effect some change in the body of the wearer and/or components thereof (e.g., to denature, destroy, or otherwise alter some analyte in the subsurface vasculature of the wearer that has a negative health effect on the wearer, e.g., a cancer cell). In some examples, the wearable device 100f could include a high-strength magnet configured to attract magnetic particles in a lumen of subsurface vasculature proximate to the high-strength magnet, and the photodetector 130g and light emitters 151g, 152g or some other sensor(s) of the wearable device 100g could be configured to detect alignment of the subsurface vasculature (i.e., the target) with the high-strength magnet such that magnetic fields emitted by the high-strength magnet can act to attract, collect, or otherwise exert magnetic forces on the magnetic particles. Other configurations, operations, and applications of wearable devices, and alignments with component(s) of such wearable devices to enable or otherwise affect such operations and/or applications, are anticipated.

Figure 1H:
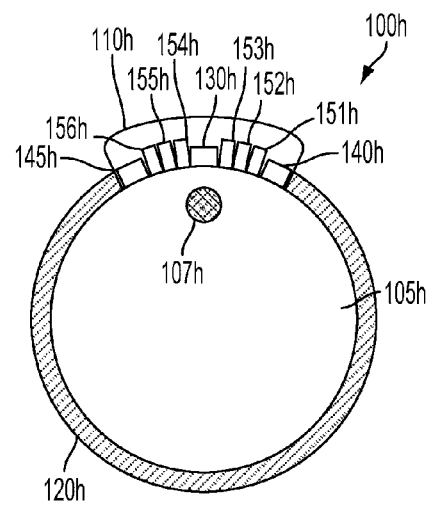
FIG. 1H is a cross-sectional view of an example wearable device while on a human wrist and while sensors of the example wearable device are aligned with a target in the wrist.

A wearable device could include a plurality of light emitters and/or sensors configured in a variety of ways to enable detection of alignment of a target relative to the plurality of light emitters, sensors, and/or other component(s) of the wearable device. FIG. 1H illustrates such a wearable device 100h. FIG. 1H is a partial cross-sectional view through a human wrist 105h illustrating an example wearable device 100h when mounted to the human wrist 105h. The wearable device 100h could be configured similarly to the wearable devices 100a, 100b, 100c, 100d, 100e, 100f, 100g of FIGS. 1A, 1B, 1C, 1D, 1E, 1F, and 1G, and includes a housing 110h (e.g., a water-resistant and/or water-proof housing) configured to contain electronic components and to be mounted to an external body surface of a wearer by a mount 120h. The mount 120h can be a band configured to enclose the wrist 105h and to position a plurality of sensors 130h, 140h, 145h and light emitters 151h, 152h, 153h, 154h, 155h, 156h in the housing 110h proximate to a target 107h (i.e., a portion of subsurface vasculature) in the wrist 105h.

As illustrated in FIG. 1H, the target 107h is located beneath the housing 110e, at a location proximate to the sensors 130h, 140h, 145h and light emitters 151h, 152h, 153h, 154h, 155h, 156h. In some embodiments, the sensors 130h, 140h, 145h and light emitters 151h, 152h, 153h, 154h, 155h, 156h could be configured to determine the location of the target 107h relative to the sensors 130h, 140h, 145h and light emitters 151h, 152h, 153h, 154h, 155h, 156h, the housing 110h, or some other element(s) of the wearable device 100h. That is, detecting alignment of the target 107h could include operating the sensors 130h, 140h, 145h and light emitters 151h, 152h, 153h, 154h, 155h, 156h to detect the location, orientation, or some other information about the disposition of the target 107h. In some embodiments, the illustrated location of the target 107h relative to the sensors 130h, 140h, 145h and light emitters 151h, 152h, 153h, 154h, 155h, 156h, housing 110h, and/or other components of the wearable device 100h could be one of one or more specified locations, such that the target 107h is aligned relative to element(s) of the wearable device 100h. Thus, the sensors 130h, 140h, 145h and light emitters 151h, 152h, 153h, 154h, 155h, 156h could be operated as described above to detect the location, orientation, or some other information about the target 107h and a determination that the target 107h is aligned could be made based on such detected information. Additionally or alternatively, the sensors 130h, 140h, 145h and light emitters 151h, 152h, 153h, 154h, 155h, 156h could be configured to detect some categorical and/or qualitative information about the alignment of the target 107h. For example, the sensors 130h, 140h, 145h and light emitters 151h, 152h, 153h, 154h, 155h, 156h could be configured to detect that the alignment of the target 107h corresponds to one of a discrete set of states, e.g., 'aligned,' 'nearly aligned,' 'not aligned,' 'aligned with a first sensor 130h,' 'aligned with a second sensor 140h,' 'aligned with a second light emitter 152h,' 'aligned with a fourth light emitter 154h,' 'not aligned between a first set of two sensors 130h, 140h,' 'not aligned between a first pair of light emitters 152h, 153h,' 'not aligned between a second pair of light emitters 153h, 154h,' etc. That is, in some examples the disposition of the target 107h relative to component(s) of the wearable device 100h could be such that the target 107h is not aligned.

Note that the sets of sensors 130g, 130h, 140h, 145h and light emitters 151g, 512g, 151h, 152h, 153h, 154h, 155h, 156h of the illustrated wearable devices 100g, 100h are disposed as linear arrays. This could be advantageous in certain applications. For example, applications wherein alignment of a wearable device and/or components thereof is more sensitive to motion of the wearable device in one direction relative to the target than in a perpendicular direction (e.g., when the target is a long object, e.g., a portion of subsurface vasculature). Other applications wherein a linear arrays of sensors and/or light emitters could be advantageous include applications wherein adjustment of and/or motion between the target and the wearable device is largely constrained to a single direction/degree of freedom (e.g., when the wearable device is mounted to a protruding element of a wearer's anatomy (e.g., a wrist, and ankle, a limb)). However, many applications are anticipated wherein an array of two or more alignment- or other property-sensing sensors and/or light emitters are arranged in 2-dimensional patterns (e.g., rectangular, hexagonal, triangular, or other regularly or irregularly spaced grids, tessellations, or other patterns). Such 2-dimensional arrays of sensors could be further configured and/or operated to detect information about a target and/or about a wearer in addition to information about alignment of the target. For example, a 2-dimensional array of sensors and/or light emitters could be operated to detect a pattern, size, or other information about subsurface vasculature, nerves, or other anatomical or physiological elements of a wearer.

Further, individual sensors and/or light emitters in an array of sensors and/or light emitters could be discrete sensors (e.g., sensors composed of individual discrete photodetectors, photodiodes, LEDs, thermistors, micro-cameras, or other discrete components and/or sensors) or light emitters (e.g., light emitters composed of individual discrete LEDS, semiconductor lasers, VCSELs) or could be part of a single chip, multi-chip module, lithographed element, or other composite element or device. Further, an array of sensors and/or light emitters could include a combination of discrete sensor and/or light emitter components and multi-sensor and/or multi-light-emitter integrated components. For example, an array of sensors and/or light emitters could include a single-chip array of VCSELs, a linear or planar CCD array, an array of PZT or other acoustic and/or piezo-electric transducers, or some other element that includes multiple sensors and/or light emitters. The sensors and/or light emitters in an array of sensors and/or light emitters could be substantially identical, or could include two or more types of sensors and/or light emitters. Some or all of the sensors and/or light emitters in an array of sensors and/or light emitters could be configured and/or operated to detect alignment of a target; further, some or all of the sensors and/or light emitters could be configured and/or operated to detect other information about a wearer and/or a target on or within the wearer.

A wearable device (e.g., 100a, 100b, 100c, 100d, 100e, 100f, 100g, 100h) could be operated based on a detected alignment of a target (e.g., a portion of subsurface vasculature). For example, one or more sensors and/or light emitters of the wearable device could be operated to detect a property of the target when the alignment of the target is detected. The one or more sensors could be sensors additionally used to detect the alignment of the target or could be different sensors. In some examples, the sensors and/or light emitters could be operated 'opportunistically,' i.e., operated during time periods during which movements of the target, the wearer, the wearable device, and/or components of the wearable device result in alignment of the target and/or other elements of interest on or within the body of the wearer with one or more sensors or other elements of the wearable device. In some examples, accelerometers, optic flow sensors, or other devices of the wearable device could be operated to allow the location and/or other information about the disposition of the target to be predicted based on a detected alignment of the target detected during a previous time period. This predicted location and/or other information could be used to predict that the target is aligned or about to be aligned and to operate the wearable device (e.g., to detect a property of the target) based on the predicted alignment. This could be particularly advantageous in applications where a sensor has a high energy requirement and/or requires a period of time to become active and/or to make a measurement. That is, such a sensor could be maintained in a disabled and/or low-power state until the wearable device predicts that the target will be and/or is currently aligned (based on a predicted future/current alignment and/or a detected alignment using sensors and/or light emitters of the wearable device); the sensor could then be activated and/or operated to make a measurement.

Additionally or alternatively, a wearable device could be configured and/or operated to align one or more components and/or to indicate an alignment to a user such that the target is aligned with one or more components of the wearable device. This could include the wearable device including servos or other actuators configured to control a location of one or more components of the wearable device relative to the target (e.g., the example wearable device 200 illustrated in FIGS. 2A and 2B). Additionally or alternatively, this could include the wearable device indicating to a wearer an adjustment of the location of the wearable device and/or of some subcomponent of the wearable device to align one or more components of the wearable device relative to the target (e.g., the example wearable device 300 illustrated in FIGS. 3A, 3B, 3C, and 3D).

Figure 2A:
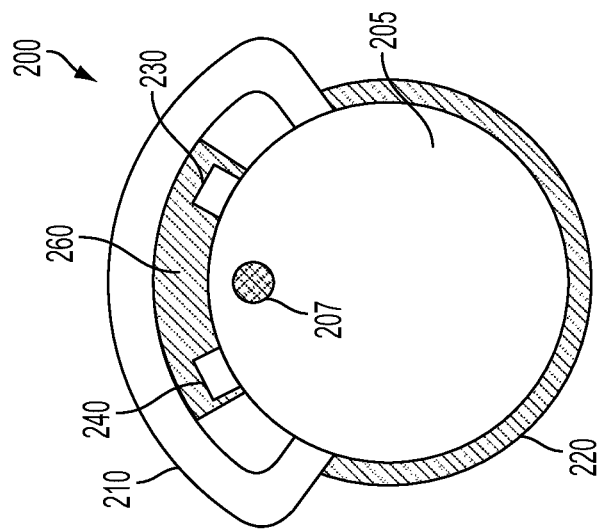
FIG. 2A is a cross-sectional view of an example wearable device while on a human wrist.
Figure 2B:
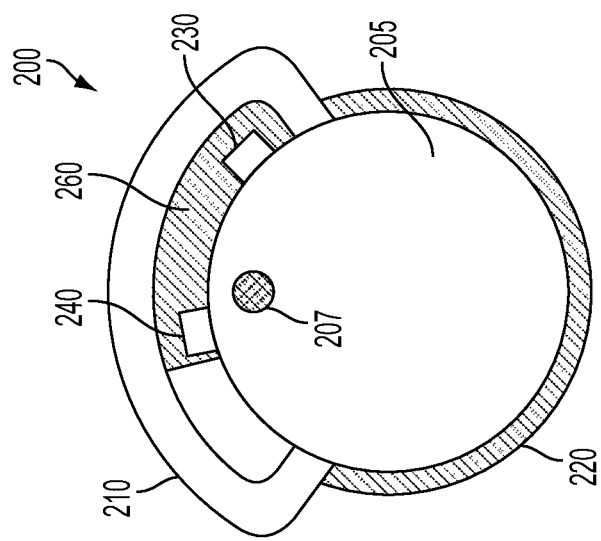
FIG. 2B is a cross-sectional view of the example wearable device illustrated in FIG. 2A while on a human wrist and while two sensors of the example wearable device are aligned with a target in the wrist.

FIGS. 2A and 2B are partial cross-sectional views through a human wrist 205 illustrating an example wearable device 200 when mounted to the human wrist 205. The wearable device 200 includes a housing 210 (e.g., a water-resistant and/or water-proof housing) configured to contain electronic components and to be mounted to an external body surface of a wearer by a mount 220. The mount 220 can be a band configured to enclose the wrist 205 and to position first 230 and second 240 sensors in the housing 210 proximate to a target 207 (i.e., a portion of subsurface vasculature) in the wrist 205. The first 230 and second 240 sensors are disposed in a sensor carriage 260 that is disposed within the housing 210 and that can be moved (e.g., by a servo, piezoelectric element, solenoid, or some other electrical and/or mechanical actuator) to control the location of the first 230 and second 240 sensors. The wearable device 200 includes additional elements that are not shown, e.g., electronics configured to operate the first 230 and second 240 sensors, to operate actuators to control to location of the sensor carriage 260, and to enable applications and/or functions of the wearable device 200, a rechargeable battery configured to power the wearable device 200, or other components. Components of the wearable device 200 could be disposed on or within the housing 210, the mount 220, or some other elements of the wearable device 200 (not shown); e.g., a second housing.

As illustrated in FIG. 2A, the target 207 is located beneath the housing 210, at a location between the first 230 and second 240 sensors. In some embodiments, the first 230 and second 230 sensors could be configured to determine the location of the target 207 relative to the sensors 230, 240, the sensor carriage 260, the housing 210, or some other element(s) of the wearable device 200. That is, detecting alignment of the target 207 could include operating the sensors 230, 240, to detect the location, orientation, or some other information about the disposition of the target 207. As illustrated in FIG. 2B, the location of the sensor carriage 260 has been controlled (e.g., by the wearable device operating a servo, motor, piezoelectric element, or other actuator) such that the sensor 230, 240 are aligned (i.e., equidistant from) the target 207.

Controlling the location of the sensor carriage 260 (and thus of the sensors 230, 240) could be performed continuously, at one or more specified periods of time, or according to some other consideration or combination of considerations. For example, a measurement of a property of the target 207 and/or of the wearer could be contingent upon alignment of the sensor 230, 240 with the target 207 and could be performed at one or more specified points in time. The sensor carriage 260 could be located to align with the target 207 during the one or more specified points in time and allowed to become un-aligned (e.g., by controlled or uncontrolled motions of the target 207, the wearer, the wearable device 200, the sensor carriage 260, or some other element or elements) at times other than the one or more specified points in time. Additionally or alternatively, the sensors 230, 240 could be continuously and/or periodically operated to detect the alignment of the target 207 and the location of the sensor carriage 260 could be responsively operated. In some examples, this could include continuously controlling the location of the sensor carriage 260 to align the target 207 with the sensors 230, 240 and/or other components of the wearable device 200. In some examples, this could include controlling the location of the sensor carriage 260 to align the target 207 with the sensors 230, 240 and/or other components of the wearable device 200 when the detected alignment has decreased below some threshold (e.g., the detected alignment is more that 5 mm away from a specified alignment). Other operations of the wearable devices as describe herein will be evident to one of skill in the art are anticipated. Further, alignment of the target 207 could include aligning the target 207 with different elements of the wearable device 200 at different points in time, and the controlled location of the sensor carriage 260 at different points in time could reflect this. Note that the sensor carriage 260 could alternatively include two or more light emitters and one or more photodetectors configured to determine the location of the target 207 relative to the two or more light emitters, the one or more photodetectors, the sensor carriage 260, the housing 210, or some other element(s) of the wearable device 200.

A wearer or other user of a wearable device (e.g., 100a, 100b, 100c, 100d, 100e, 100f, 100g, 100h, 200) could operate, dispose, adjust, or otherwise locate the wearable device and/or components thereof to align one or more components (e.g., a sensor, a light emitter) of the wearable device with a target or other component on or within the body of the wearer. The wearable device could operate two or more sensors (e.g., photodetectors, thermistors, or some other sensors) and/or two or more light emitters and one or more photodetectors configured to detect alignment of the target and could indicate (e.g., by a display, an emitted sound, a vibration, or some other indicating means) the detected alignment to the wearer or to some other user such that the wearer or other user could adjust the location of the one or more components of the wearable device with the target.

Figure 3A:
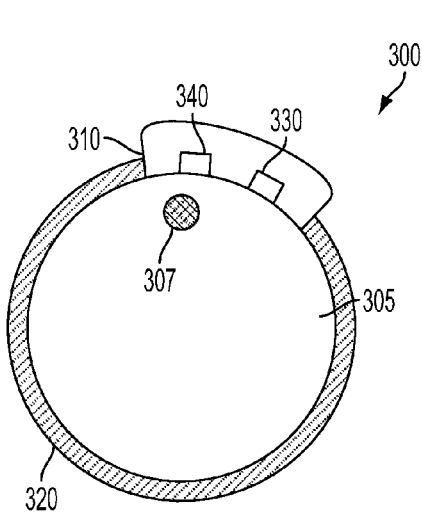
FIG. 3A is side partial cross-sectional view of an example wearable device while on a human wrist.
Figure 3B:
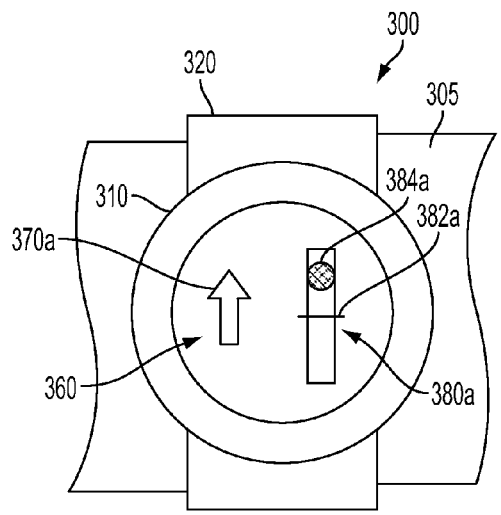
FIG. 3B is a top view of the example wearable device illustrated in FIG. 3A.
Figure 3C:
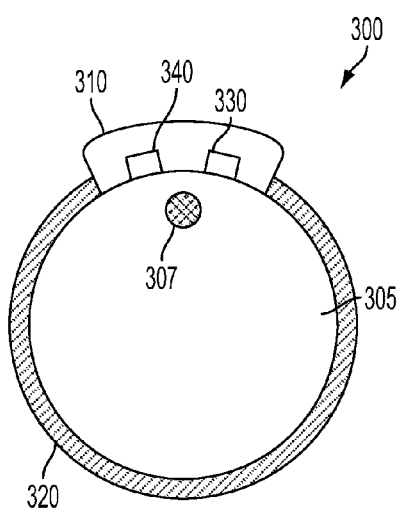
FIG. 3C is a cross-sectional view of the example wearable device illustrated in FIG. 3A while on a human wrist and while a particular sensor of the example wearable device is aligned with a target in the wrist.

FIGS. 3A and 3C are partial cross-sectional views through a human wrist 305 illustrating an example wearable device 300 when mounted to the human wrist 305. The wearable device 300 includes a housing 310 (e.g., a water-resistant and/or water-proof housing) configured to contain electronic components and to be mounted to an external body surface of a wearer by a mount 320. The mount 320 can be a band configured to enclose the wrist 305 and to position first 330 and second 340 sensors in the housing 210 proximate to a target 307 (i.e., a portion of subsurface vasculature) in the wrist 305. The wearable device 300 additionally includes a display 360 (illustrated in top views in FIGS. 3B and 3D) configured to present information to a user and/or to receive inputs or commands from the user. The wearable device 300 includes additional elements that are not shown, e.g., electronics configured to operate the first 330 and second 340 sensors, to operate the display 350, and to enable applications and/or functions of the wearable device 300, a rechargeable battery configured to power the wearable device 300, or other components. Components of the wearable device 300 could be disposed on or within the housing 310, the mount 320, or some other elements of the wearable device 300 (not shown); e.g., a second housing.

As illustrated in FIG. 3A, the target 307 is located beneath the housing 310, at a location between the first 330 and second 340 sensors. In some embodiments, the first 330 and second 330 sensors could be configured to determine the location of the target 307 relative to the sensors 330, 340, the housing 310, or some other element(s) of the wearable device 300. That is, detecting alignment of the target 307 could include operating the sensors 330, 340, to detect the location, orientation, or some other information about the disposition of the target 307. Correspondingly, the display 360 (as shown in FIG. 3B) could be operated to present a relative alignment display 370a indicating that the target 307 is not aligned, and that the wearer could adjust the wearable device 300 in the indicated direction in order to align the wearable device 300 with the target 307. Additionally or alternatively, the display 360 could be operated to present an absolute alignment display 380a including an alignment indicator 384a having a distance and direction from an alignment mark 382a indicating a degree and direction to which the target 307 is not aligned, and that the wearer could adjust the wearable device 300 in the indicated direction by the indicated amount in order to align the wearable device 300 with the target 307.

Figure 3D:
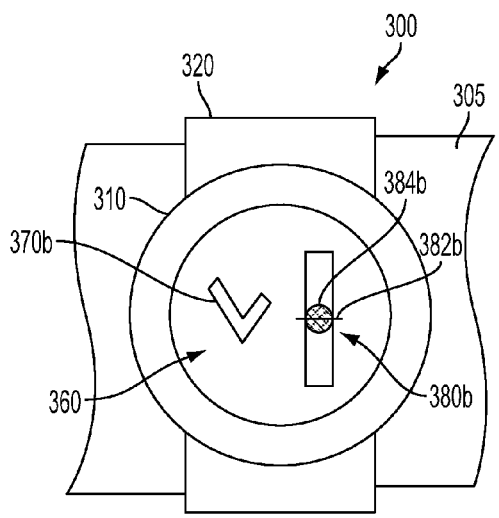
FIG. 3D is a top view of the example wearable device illustrated in FIG. 3C.

As illustrated in FIG. 3C, the target 307 is located beneath the housing 310, at a location midway between the first 330 and second 340 sensors such that the target 307 is aligned with the wearable device 300. Correspondingly, the display 360 (as shown in FIG. 3D) could be operated to present a relative alignment display 370a indicating that the target 307 is aligned. Additionally or alternatively, the display 360 could be operated to present an absolute alignment display 380b including an alignment indicator 384b whose substantially overlap with an alignment mark 382b indicates that the target 307 is aligned.

Indicating alignment (e.g., presenting the relative 370a/b and/or absolute 380a/b alignment display and/or using some other method of indication) could be performed continuously, at one or more specified periods of time, or according to some other consideration or combination of considerations. For example, a measurement of a property of the target 307 and/or of the wearer could be contingent upon alignment of the sensors 330, 340 with the target 307 and could be performed at one or more specified points in time. The display 360 or other components of the wearable device 300 could be operated to indicate the alignment and/or to instruct the wearer to perform an adjustment of the location of the wearable device 300 during the one or more specified points in time and allowed to become un-aligned (e.g., by controlled or uncontrolled motions of the target 307, the wearer, the wearable device 300, or some other element or elements) at times other than the one or more specified points in time. Additionally or alternatively, the sensors 330, 340 could be continuously and/or periodically operated to detect the alignment of the target 307 and the display 360 could be responsively operated to indicate an adjustment and/or alignment. In some examples, this could include continuously presenting the relative 370a/b and/or absolute 380a/b alignment display and/or indicating an adjustment or alignment by some other means. In some examples, this could include presenting the relative 370a/b and/or absolute 380a/b alignment display and/or indicating an adjustment or alignment by some other means when the detected alignment has decreased below some threshold (e.g., the detected alignment is more that 5 mm away from a specified alignment). Other operations of the wearable devices as describe herein will be evident to one of skill in the art are anticipated. Further, alignment of the target 307 could include aligning the target 307 with different elements of the wearable device 300 at different points in time, and the indication of alignment (using, e.g., the display 360) could reflect this.

Note that the indications shown in FIGS. 3B and 3D are exemplary, and not intended to be limiting. A wearable device could present different or additional indications on a display related to the alignment of a target. A display of a wearable device could additionally be operated to present additional or alternate information to a wearer. Further, a display of a wearable device could have a different shape or include additional or alternative elements. For example, an array of LEDs or other light emitters could be included in a wearable device and could be operated to indicate information about alignment of a target relative to one or more components of the wearable device such that a wearer could adjust the wearable device to align the target. Alternate methods could be employed to indicate alignment information to a wearer, including vibration (e.g., using a vibrator motor in the wearable device), sound (e.g., using speakers and/or piezo elements of the wearable device), or some other method. In some examples, the wearable device could include a wireless transceiver or some other means of communication configured to transmit alignment information to another device (e.g., a smartphone, a robotic actuator) and the other device could indicate the alignment information (e.g., using a display of the other device) and/or adjust the location of components of the wearable device (e.g., by manipulating the wearable device and/or components thereof using a robotic actuator).

Note that FIGS. 3A and 3C illustrate adjustment of the wearable device 300 taking the form of rotation of the entire wearable device 300 about the wrist 305. This is a non-limiting example of an adjustment of a wearable device and/or components thereof that could be effected by a wearer or other user in response to indication of an adjustment and/or alignment. In some examples, adjustment by the wearer could include repositioning a wearable device in some other way (e.g., by moving the device up or down the limb of the wearer). In some examples, adjustment by the wearer could include manipulating and/or reconfiguring some mechanism(s) of the wearable device to align one or more components of the wearable device with the target according to some indication of the wearable device. In some examples, the wearable device could indicate other adjustments and/or reconfigurations to be performed by the wearer (e.g., application and/or rotation of a filter, reconfiguring the wearable device into a different mechanical or other configuration related to a different operational mode of the wearable device).

Note that the wearable device 300 could additionally or alternatively include two or more light emitters and one or more photodetectors configured to determine the location of the target 307 relative to the two or more light emitters, the one or more photodetectors, the housing 310, or some other element(s) of the wearable device 300.

Note that the alignment of the targets (e.g., 207, 307), as well as the control and/or adjustment of the location of one or more sensors or other components (e.g., 230, 240, 331, 332, 333, 334, 335, 336, 350), as illustrated in FIGS. 2A, 2B, 3A and 3C, is one-dimensional. That is, the location of the sensors and other components of the illustrated example wearable device (e.g., 200, 300) is only illustrated as being controlled in one direction. It is anticipated that control of the location of sensors, light emitters, or other components of a wearable device to align such sensors or other components could be controlled in two or more dimensions, according to an application. In some examples, this could include a wearable device being configured to control the location of sensors, light emitters, or other components (e.g., using servos or other actuators) in two or more dimensions. In some examples, this could include a wearable device indicating to a wearer or other user to adjust the location of the wearable device and/or one or more components thereof in two or more dimensions (e.g., the wearable device could be mounted around a wrist of the wearer, and the wearable device could indicate a rotation of the wearable device about the wrist and a displacement of the wearable device toward or away from the end of the limb). In some examples, a wearable device could be configured to control the location of (e.g., by operating a servo or other actuator) one or more components of the wearable device (e.g., a sensor, a light emitter) and to indicate to a wearer or other user some adjustment of the wearable device or components thereof to effect alignment of a target with the wearable device.

Note that example devices herein are configured to be mounted to and to align with targets within a wrist of a wearer. However, the embodiments described herein could be applied to other body parts (e.g., an ankle, a thigh, a chest, a forehead, a thigh, a finger), or to detect alignment of targets in other environments. For example, embodiments described herein could be applied to detect the alignment of a target (e.g., a fluid conduit, a tube, a sample container, an analyte-attracting and/or concentrating device) in an environment (e.g., a natural environment, an environment of an industrial, pharmaceutical, or water treatment process) relative to some apparatus using two or more sensors of the apparatus.

Sensors and/or detectors as described herein could include a wide variety of components configured to detect properties of a wide variety of physical parameters. Sensors and/or detectors could include photodetectors, temperature sensors, visible light sensors, infrared sensors, ultraviolet sensors, cameras, force transducers, acoustical transducers, piezo elements, electromagnetic field sensors, radiation sensors, electrical current and/or voltage sensors, magnetic field sensors, electric field sensors, or any other sensors or combinations of sensors that could be configured to detect some information about the alignment of a target relative to the sensors and/or to one or more components of a device comprising the sensors. Photodetectors could be configured to detect one or more properties of light received from a target and/or an environment containing the target and could include photodiodes, phototransistors, active pixel sensors, CCD sensors, or some other light-sensitive elements. Photodetectors could be configured to detect a color, an intensity, a wavelength, a spectrum, a polarization, or some other property or properties of received light.

Sensors and/or detectors as described herein could additionally include and/or be configured to operate in concert with energy emitters. Energy emitters could include light emitters, infrared emitters, ultraviolet emitters, acoustical and/or ultrasonic emitters, electromagnetic field emitters, microwave emitters, heaters, or some other components configured to emit and/or direct energy toward a target and/or an environment containing a target. Light emitters could include LEDs, lasers, VCSELs, or other elements and could be configured to emit light having one or more specified properties. For example, the target could be subsurface vasculature beneath skin of a wearer, and the emitted light could have a specified wavelength (e.g., 400 nanometers) such that the emitted light minimally interacts with tissue of the wearer other than blood in the subsurface vasculature.

The sensors and/or detectors could be operated to detect one or more of a variety of properties of a wearer of the wearable device via an external body surface of the wearer e.g., by contacting, directing energy (e.g., electrical, magnetic, illumination, acoustic waves) through/into, detecting energy (e.g., electrical, magnetic, illumination, acoustic waves) received from/through, or otherwise interacting with and/or through an external body surface of the wearer (i.e., skin of the wearer's wrist). For example, light could be emitted toward an external body surface of a wearer to illuminate the external body surface, and one or more properties of light received from the external body surface could be detected (e.g., using the photodiode). This illumination and detection could be used to detect an oxygenation state of blood proximate to the wearable device (e.g., in a portion of subsurface vasculature), a heart rate of the wearer, a flow profile of the blood in vasculature of the wearer, or some other information. The sensors could be configured to detect one or more properties of a contrast agent (e.g., a functionalized fluorophore, chromophore, magnetic particle, or some other natural or artificial contrast agent) in the body of the wearer according to an application.

In some examples, sensors of a device could be configured to detect alignment of a target by detecting the location, orientation, alignment, and/or other information about the disposition of an alignment feature. An alignment feature could be any element(s) within or on the surface of the body of a wearer that has a predictable and/or stable spatial relationship with a target. For example, an alignment feature could be a tendon, nerve, or other anatomical feature that is proximate to a portion of subsurface vasculature (i.e., a target). The alignment feature could have a known and/or specified spatial relationship with the target and/or the spatial relationship between the alignment feature and the target could be determined by a wearable device using sensors of the wearable device. Note that references herein to a wearable or other device detecting alignment of a target could equally apply to the wearable or other device detecting the location, orientation, alignment and/or other information about the disposition of an alignment feature.

The alignment feature could be artificial. The alignment feature could be a pigment applied to the surface and/or within the skin of a wearer. For example, the alignment feature could be a tattoo. The alignment feature could be an implanted device or object(s). One or more properties of the alignment feature could enable detection of the location, orientation, alignment, or other disposition information about the alignment feature. For example, the alignment feature could include fluorescent pigments or coatings and/or pigments or surface treatments having a specified color. The alignment feature could have a specified shape or geometry to enable detection of the alignment feature and/or detect a location on or within the alignment feature. For example, the alignment feature could be a tattoo applied around the wrist of a wearer and including a series of gray-coded or otherwise spatially-encoded bars or other features such that a device mounted to the wrist could determine the alignment of the device relative to elements of the wrist (e.g., bones, blood vessels, tendons, nerves) based on the patterns of the tattoo detected by the device. The alignment feature could be applied and/or inserted in the body of a wearer such that is has a specified spatial relationship with a target and/or the spatial relationship between a target and the alignment feature could be determined after application and/or insertion. Other embodiments and/or applications of natural (e.g., anatomical) and artificial alignment features are anticipated.

Wearable devices and other embodiments as described herein can include a variety of components configured in a variety of ways. Devices described herein could include electronics including a variety of different components configured in a variety of ways to enable applications of the wearable device. The electronics could include controllers, amplifiers, switches, display drivers, touch sensors, wireless communications chipsets (e.g., Bluetooth radios or other radio transceivers and associated baseband circuitry to enable wireless communications between the wearable device and some other system(s)), or other components. The electronics could include a controller configured to operate one or more sensors and/or components of sensors to detect alignment of a target and/or one or more properties of the body of the wearer. The controller could include a processor configured to execute computer-readable instructions (e.g., program instructions stored in data storage of the wearable device) to enable applications of the wearable device. The electronics can include additional or alternative components according to an application of the wearable device.

Wearable devices as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the wearable device, to determine some property of the wearable device and/or of the wearer of the wearable device (e.g., an alignment of a target relative to one or more components of the wearable device), or to provide some other functionality or application to the wearer and/or user. As one example, the user interface could be operated to indicate information about the alignment of a target to the wearer. As another example, the wearer could press an indicated region of the user interface to indicate that the wearable device should begin logging detected medical information about the wearer. Other indicated information, changes in operation of the wearable device, or other functions and applications of the user interface are anticipated.

Note that the embodiments illustrated in FIGS. 1A-H, 2A-B, and 3A-D are illustrative examples and not meant to be limiting. Alternative embodiments, including more or fewer components in alternative configurations are anticipated. A wearable device could include multiple housings or other such assemblies each containing some set of components to enable applications of such a wearable device. For example, a wearable device could include a first housing within which are disposed sensors and/or light emitters configured to detect the alignment of a target relative to the first housing/sensors and/or light emitters and a second housing containing a user interface and electronics configured to operate the sensors and/or light emitters and to present information to and receive commands from a user of the wearable device. A wearable device could be configured to perform a variety of functions and to enable a variety of applications. Wearable devices could be configured to operate in concert with other devices or systems; for example, wearable devices could include a wireless communication interface configured to transmit data indicative of one or more properties of the body of a wearer of the wearable device. Other embodiments, operations, configurations, and applications of a wearable device as described herein are anticipated.

Figure 4:
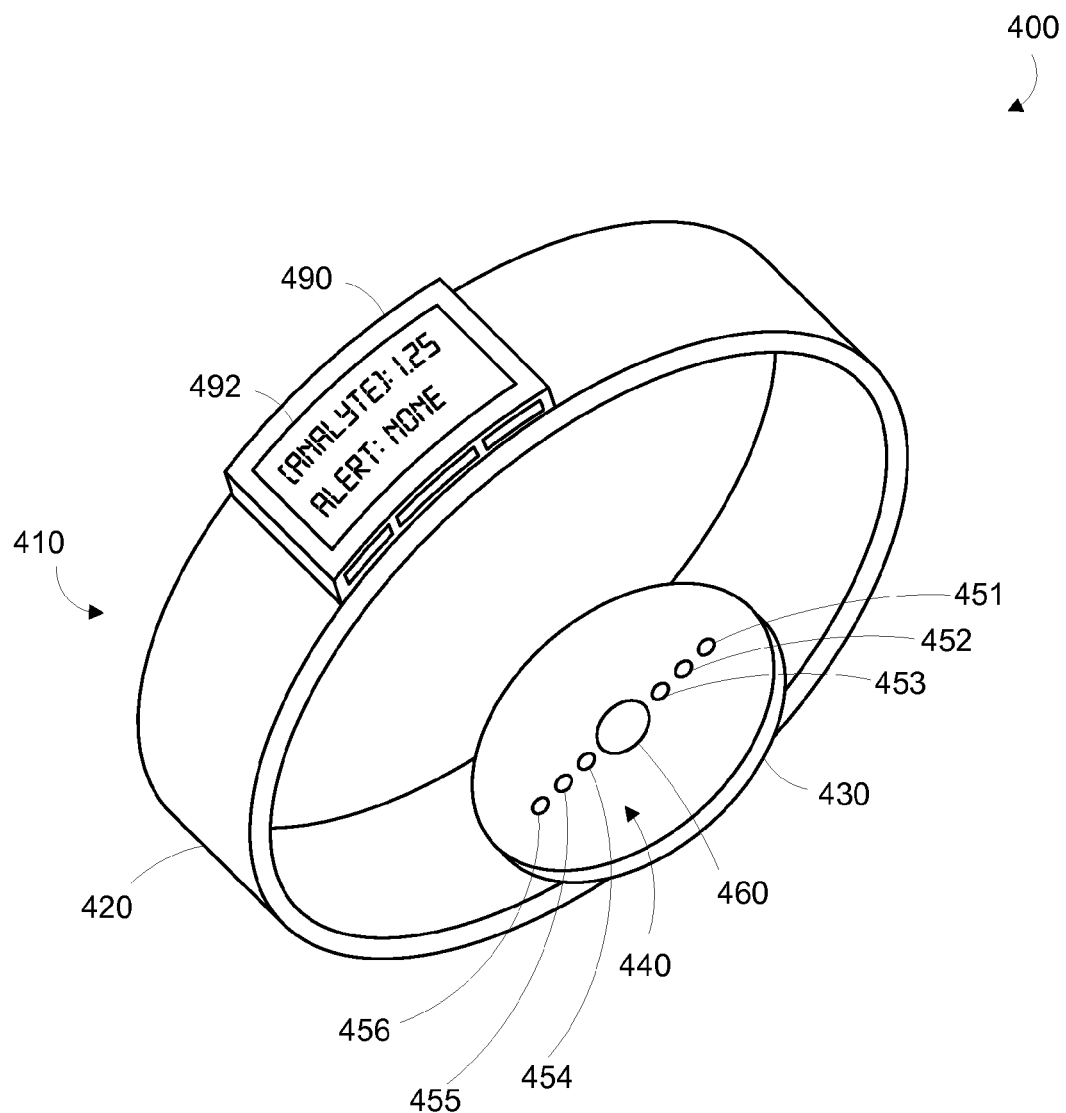
FIG. 4 is a perspective view of an example wearable device.

A wearable device 400 (illustrated in FIG. 4) can automatically detect alignment of a target relative to the wearable device 400 and/or measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or other targets or elements of the body of the wearer are easily observable, the qualification of which will depend on the type of detection system used. The device may be placed in close proximity to the skin or tissue. A mount 410, such as a belt, wristband, ankle band, etc. can be provided to mount the device at, on or in proximity to body surface. The mount 410 may prevent the wearable device from moving relative to the body to reduce measurement error and noise. In one example, shown in FIG. 4, the mount 410, may take the form of a strap or band 420 that can be worn around a part of the body. Further, the mount 410 may be an adhesive substrate for adhering the wearable device 400 to the body of a wearer.

A housing 430 is disposed on the mount 410 such that it can be positioned on the body. A contact surface 440 of the housing 430 is intended to be mounted facing to the external body surface. The housing 430 may include sensors 451, 452, 453, 454, 455, 456 for detecting the alignment of a target (e.g., a portion of subsurface vasculature) relative to the sensors 451, 452, 453, 454, 455, 456 and/or some other element(s) of the wearable device 400. The housing 430 may further include at least one further sensor 460 for detecting at least one property of the target and/or some other element on or within the body of the wearer, which could include any parameters that may relate to the health of the person wearing the wearable device. For example, the further sensor 480 could be configured to measure blood pressure, pulse rate, respiration rate, skin temperature, etc. In a non-exhaustive list, the sensors 451, 452, 453, 454, 455, 456 and further sensor 480 may include any one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. Components disposed in the housing 430 may be miniaturized so that the wearable device may be worn on the body without significantly interfering with the wearer's usual activities. The wearable device additionally includes electronics configured to enable functions of the wearable device 400 including operating the sensors 451, 452, 453, 454, 455, 456 to detect alignment with a target on or within the body of a wearer. Alternatively, the illustrated 451, 452, 453, 454, 455, 456 could be light emitters and the illustrated 460 could be a photodetector configured detect the alignment of the target relative to the light emitters 451, 452, 453, 454, 455, 456, photodetector 460, and/or other elements of the wearable device 400.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of the measured alignment and/or to indicate an adjustment which could be made by the wearer to align a target with the wearable device.

Figure 5A:
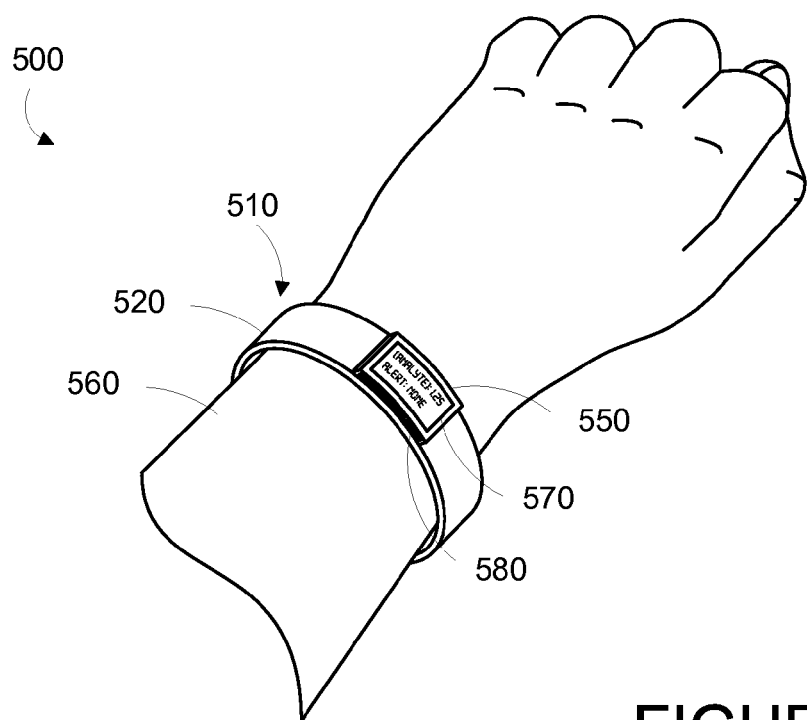
FIG. 5A is a perspective top view of an example wrist-mounted device, when mounted on a wearer's wrist.
Figure 5B:
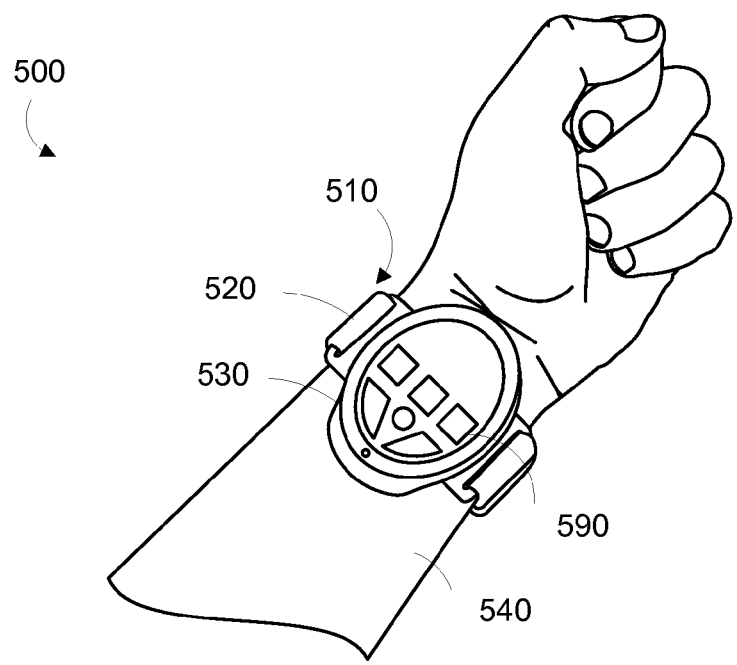
FIG. 5B is a perspective bottom view of an example wrist-mounted device shown in FIG. 5A, when mounted on a wearer's wrist.

In some examples, the wearable device is provided as a wrist-mounted device, as shown in FIGS. 5A and 5B. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a housing 530 containing a data collection system and positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the housing 530 may be located on the anterior side 540 of the wearer's wrist where the subsurface vasculature or other elements of the body of the wearer may be readily observable. However, other configurations are contemplated.

The display 570 may be configured to display a visual indication of the alert or recommendation and/or an indication of the measured alignment of a target relative to the wearable device 500. Further, the user interface 550 may include one or more buttons 580 for accepting inputs from the wearer. For example, the buttons 580 may be configured to change the text or other information visible on the display 570. As shown in FIG. 5B, housing 530 may also include one or more buttons 590 for accepting inputs from the wearer. The buttons 590 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

FIG. 6 is a simplified schematic of a system including one or more wearable devices 600. The one or more wearable devices 600 may be configured to transmit data via a communication interface 610 over one or more communication networks 620 to a remote server 630. In one embodiment, the communication interface 610 includes a wireless transceiver for sending and receiving communications to and from the server 630. In further embodiments, the communication interface 610 may include any means for the transfer of data, including both wired and wireless communications. For example, the communication interface may include a universal serial bus (USB) interface or a secure digital (SD) card interface. Communication networks 620 may be any one of may be one of: a plain old telephone service (POTS) network, a cellular network, a fiber network and a data network. The server 630 may include any type of remote computing device or remote cloud computing network. Further, communication network 620 may include one or more intermediaries, including, for example wherein the wearable device 600 transmits data to a mobile phone or other personal computing device, which in turn transmits the data to the server 630.

In addition to receiving communications from the wearable device 600, such as collected physiological parameter data and data regarding health state as input by the user and/or one or more properties of a wearer detected using a sensor disposed in the wearable device 600, the server may also be configured to gather and/or receive either from the wearable device 600 or from some other source, information regarding a wearer's overall medical history, environmental factors and geographical data. For example, a user account may be established on the server for every wearer that contains the wearer's medical history. Moreover, in some examples, the server 630 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 7:
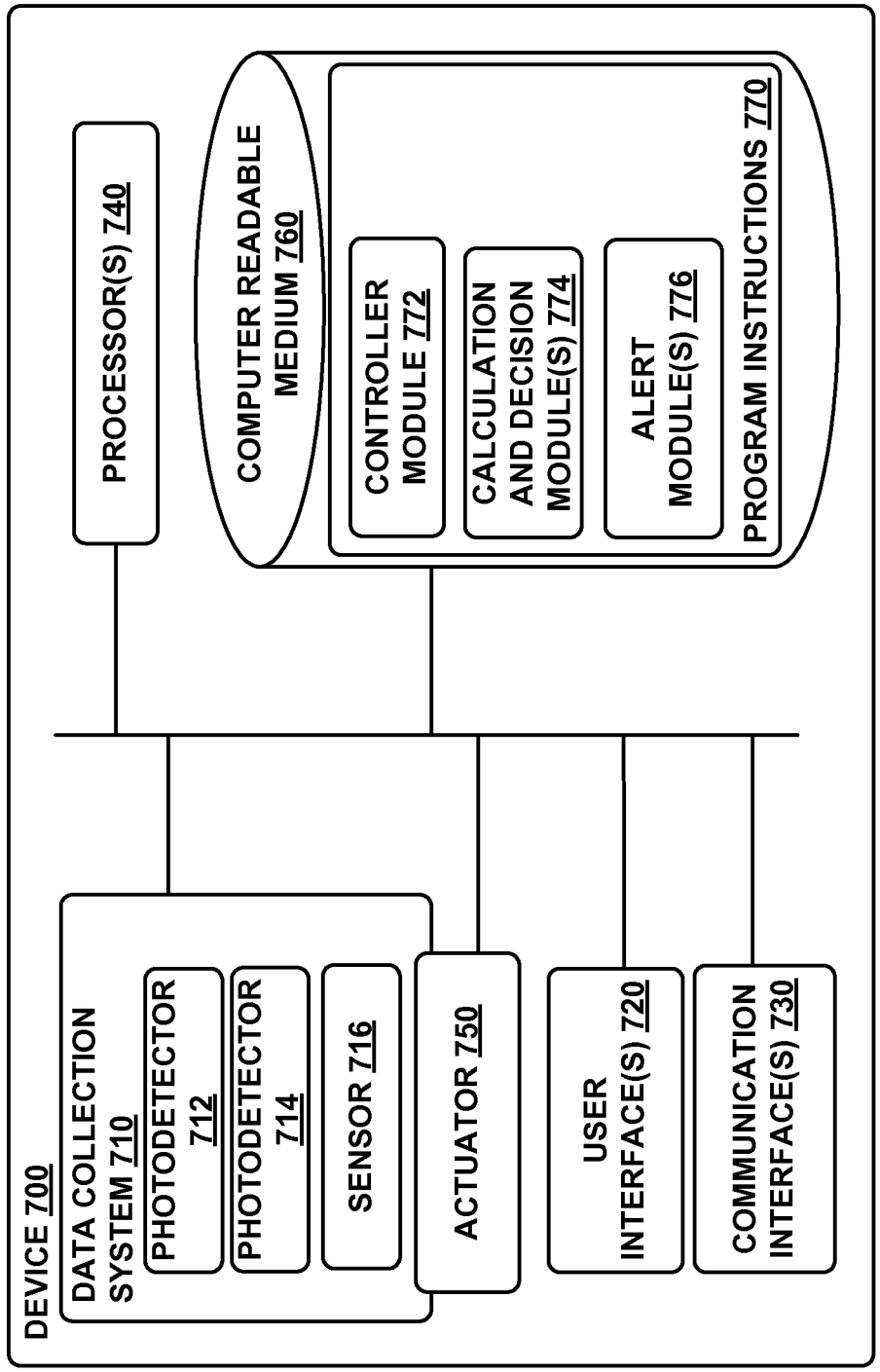
FIG. 7 is a functional block diagram of an example device.

FIG. 7 is a simplified block diagram illustrating the components of a device 700, according to an example embodiment. Device 700 may take the form of or be similar to one of the wearable devices 100a, 100b, 100c, 100d, 100e, 100f, 100g, 100h, 200, 300, 400, 500 shown in FIGS. 1A-H, 2A-B, 3A-D, 4, and 5A-B. However, device 700 may also take other forms, such as an ankle, waist, or chest-mounted device. Device 700 could also take the form of a device that is not configured to be mounted to a body. For example, device 700 could take the form of a handheld device configured to be maintained in proximity to an environment of interest (e.g., a body part, a biological sample container, a volume of a water treatment system) by a user or operator of the device 700 or by a frame or other supporting structure. Device 700 also could take other forms.

In particular, FIG. 7 shows an example of a device 700 having a data collection system 710 that includes two photodetectors 712, 714 and a sensor 716, an actuator 750, a user interface 720, communication interface 730 for transmitting data to a remote system, A processor 740 and a computer readable storage medium 760. The components of the device 700 may be disposed on a mount or on some other structure for mounting the device to enable stable detection of one or more properties of an environment of interest (e.g., of a body of a wearer of the device 700) and/or detection of the alignment of a target within the environment of interest, for example, to an external body surface where a portion of subsurface vasculature or other anatomical element (i.e., a target) is readily observable.

Processor 740 may be a general-purpose processor or a special purpose processor (e.g., digital signal processors, application specific integrated circuits, etc.). The one or more processors 740 can be configured to execute computer-readable program instructions 770 that are stored in the computer readable medium 760 and that are executable to provide the functionality of a device 700 described herein.

The computer readable medium 760 may include or take the form of one or more non-transitory, computer-readable storage media that can be read or accessed by at least one processor 740. The one or more computer-readable storage media can include volatile and/or non-volatile storage components, such as optical, magnetic, organic or other memory or disc storage, which can be integrated in whole or in part with at least one of the one or more processors 740. In some embodiments, the computer readable medium 760 can be implemented using a single physical device (e.g., one optical, magnetic, organic or other memory or disc storage unit), while in other embodiments, the computer readable medium 760 can be implemented using two or more physical devices.

Photodetectors 712, 714 could include any light-detecting components configured to detect the location, orientation, alignment, and/or some other information about the disposition of a target (e.g., a portion of subsurface vasculature) relative to one or more components (e.g., the photodetectors 712, 714, the sensor 716) of the device 700. Sensor 716 could include one or more components configured to detect one or more properties of an environment proximate to the sensor 716 (e.g., a portion of subsurface vasculature) and/or of energy or matter received from the proximate environment. As described above, the photodetectors 712, 714 and the sensor 716 may include any component or components capable of detecting at least one property, which could include any properties that may relate to the alignment and/or some other property of the target and/or of the environment being analyzed by the device (e.g., the body of the wearer or a subsection thereof). For example, the sensor 716 could be configured to measure blood pressure, pulse rate, skin temperature, etc. In some examples, the photodetectors 712, 714 and/or the sensor 716 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. In examples wherein the photodetectors 712, 714 and/or the sensor 716 include a light sensor, the light sensor could be a photodiode, a photomultiplier, a CCD, a photocell, a photoresistive element, a camera, or any other sensor or sensors configured to detect one or more properties of light received from the target and/or an environment containing the target.

The photodetectors 712, 714 and/or the sensor 716 could additionally include a light source or other energy emitter for transmitting illumination or other energy that can illuminate and/or penetrate the environment to illuminate, excite, or otherwise affect one or more elements of interest on or in the target and/or the environment containing the target. The wavelength of transmitted illumination could be specified to penetrate biological tissues of a wearer; for example, the transmitted illumination could have a wavelength within a near-infrared (NIR) transparency window of biological tissue. The wavelength of the transmitted illumination could be specified to be a wavelength that causes fluorescence and/or emission of light by fluorophores, chromophores, or other elements of interest. An energy emitter of the photodetectors 712, 714 and/or the sensor 716 could be configured to produce other forms of energy toward the environment proximate to photodetectors 712, 714 and/or the sensor 716 that could result in emission, reflection, scattering or some other generation of light or other energy or matter by other chemicals, imaging agents, biological elements, or other analytes proximate to the photodetectors 712, 714 and/or the sensor 716.

Additionally or alternatively, the data collection system 710 could include two or more light emitters and one or more photodetectors configured to detect the alignment of a target relative to the photodetector and/or light emitters as described herein. Such a data collection system 710 could be further configured to detect one or more properties (e.g., a concentration of an analyte, an oxygen saturation) of the target and/or of the body of the wearer.

The actuator 750 could be any electrical and/or mechanical device configured to control the location of the data collection system 710 and/or of individual elements (e.g., 712, 714, 716) of the data collection system 710. The actuator 750 could include servos, piezoelectric elements, solenoids, motors, or other force-transducing elements.

The program instructions 770 stored on the computer readable medium 760 may include instructions to perform any of the methods described herein. For instance, in the illustrated embodiment, program instructions 770 include a controller module 772, calculation and decision module 774 and an alert module 776.

The controller module 772 can include instructions for operating the photodetectors 712, 714 and/or the sensor 716. For example, the controller 772 may operate a light source and/or light sensors of the photodetectors 712, 714 and/or the sensor 716 during each of a set of pre-set measurement periods. The controller module 772 can further include instructions for operating the actuator 750 to control the location of the of the data collection system 710 and/or of individual elements (e.g., 712, 714, 716) of the data collection system 710. For example, the controller module 772 could include instructions to operate the actuator 750 to control the location of one or more elements of the data collection system 710 such that the one or more elements of the data collection system 710 are aligned with a target. This operation of the actuator 750 could be performed responsive to an alignment of the one or more elements of the data collection system 710 relative to the target as detected by the photodetectors 712, 714.

The controller module 772 can also include instructions for operating a user interface 720. For example, controller module 772 may include instructions for displaying data collected by the data collection system 710 and analyzed by the calculation and decision module 774, or for displaying one or more alerts generated by the alert module 776. Controller module 772 may include instructions for displaying data related to a detected alignment of one or more elements of the device 700 such that a user could adjust the location and/or configuration of the device such that the one or more elements of the device 700 are aligned with the target. Further, controller module 772 may include instructions to execute certain functions based on inputs accepted by the user interface 720, such as inputs accepted by one or more buttons disposed on the user interface.

Communication platform 730 may also be operated by instructions within the controller module 772, such as instructions for sending and/or receiving information via a wireless antenna, which may be disposed on or in the device 700. The communication interface 730 can optionally include one or more oscillators, mixers, frequency injectors, etc. to modulate and/or demodulate information on a carrier frequency to be transmitted and/or received by the antenna. In some examples, the device 700 is configured to indicate an output from the processor by modulating an impedance of the antenna in a manner that is perceivable by a remote server or other remote computing device.

Calculation and decision module 774 may include instructions for receiving data from the photodetectors 712, 714 and/or the sensor 716, analyzing the data to determine one or more properties of a target (e.g., the alignment of the target relative to one or more components of the device 700) and/or an environment containing the target (e.g., of a body of a wearer of the device 700), such as concentration of a target analyte, analyzing the data to determine if a medical condition or other specified condition is indicated, or other analytical processes relating to the environment proximate to the device 700. In particular, the calculation and decision module 774 may include instructions for determining, for each preset measurement time, the presence, concentration, and/or other properties of a clinically-relevant analyte based on information detected using the photodetectors 712, 714 and/or the sensor 716; and determining whether a medical condition is indicated based on at least the corresponding presence, concentration, or other property of the clinically-relevant analyte. These instructions could be executed at each of a set of preset measurement times.

The program instructions of the calculation and decision module 774 may, in some examples, be stored in a computer-readable medium and executed by a processor located external to the device 700. For example, the device 700 could be configured to collect certain data regarding physiological parameters from the user and then transmit the data to a remote server, which may include a mobile device, a personal computer, the cloud, or any other remote system, for further processing.

The computer readable medium 760 may further contain other data or information, such as medical and health history of a user of the device 700, that may be useful in determining whether a medical condition or some other specified condition is indicated. Further, the computer readable medium 760 may contain data corresponding to certain physiological parameter baselines, above or below which a medical condition is indicated. The baselines may be pre-stored on the computer readable medium 760, may be transmitted from a remote source, such as a remote server, or may be generated by the calculation and decision module 774 itself. The calculation and decision module 774 may include instructions for generating individual baselines for the user of the device 700 based on data collected over a certain number of measurement periods. Baselines may also be generated by a remote server and transmitted to the device 700 via communication interface 730. The calculation and decision module 774 may also, upon determining that a medical or other emergency condition is indicated, generate one or more recommendations for the user of the device 700 based, at least in part, on consultation of a clinical protocol. Such recommendations may alternatively be generated by the remote server and transmitted to the device 700.

In some examples, the collected physiological parameter data, baseline profiles, health state information input by device users and generated recommendations and clinical protocols may additionally be input to a cloud network and be made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 774 that a medical or other specified condition is indicated, the alert module 776 may generate an alert via the user interface 720. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

III. Example Methods

Figure 8:
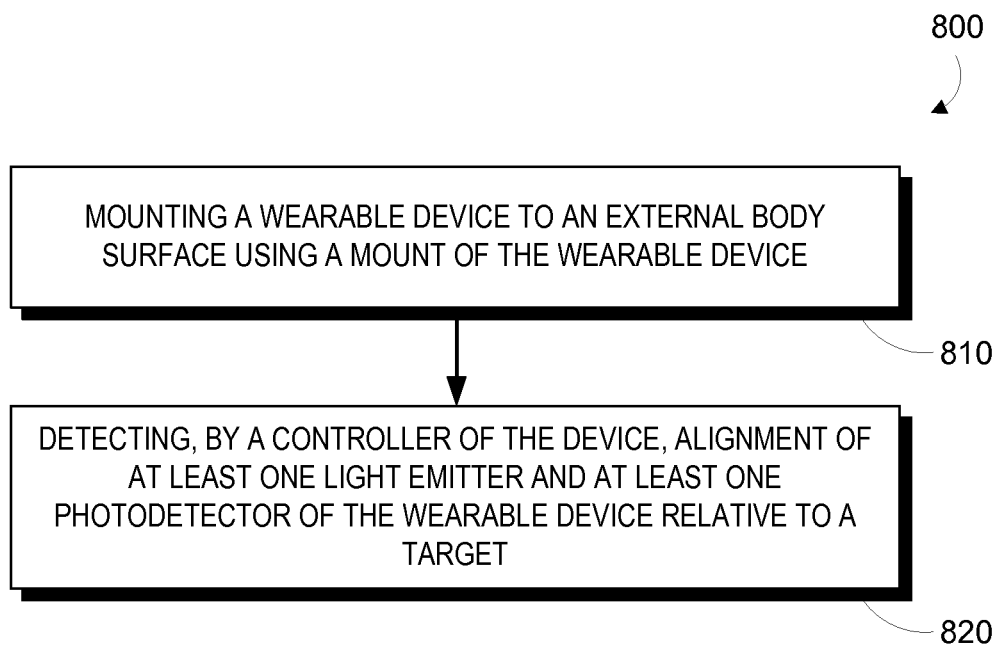
FIG. 8 is a flowchart of an example method.

FIG. 8 is a flowchart of a method 800 for operating a wearable device. The operated wearable device includes (i) at least light emitter, (ii) at least one photodetector, (iii) a mount configured to mount the at least one light emitter and at least one photodetector to an external body surface proximate to a target, and (iv) a controller configured to operate the at least one light emitter and the at least one photodetector.

The method 800 includes mounting the wearable device to an external body surface using the mount (810). In some examples, the wearable device could be configured to be mounted to a wrist of a wearer (e.g., the embodiments illustrated in FIGS. 1A-1H, 2A-B, 3A-D, 4, and 5A-B) such that the at least one light emitter and at least one photodetector can be operated to detect alignment of the target (e.g., a portion of subsurface vasculature) proximate to and/or within the wrist of the wearer. In some examples, the mount includes an adhesive, and mounting the wearable device to the external body surface (810) includes activating, applying, and/or exposing the adhesive and adhering the wearable device to the external body surface.

The method 800 also includes detecting, by the controller, alignment of the at least one light emitter and at least one photodetector relative to the target (820). In some embodiments, detecting alignment of the at least one light emitter and at least one photodetector relative to the target (820) could include operating the at least one light emitter and at least one photodetector to detect the location, orientation, or some other information about the disposition of the target. In some embodiments, the location of the target relative to the at least one light emitter, at least one photodetector, and/or other components of the wearable device could be one of one or more specified locations, such that the target is aligned relative to element(s) of the wearable device. Thus, the at least one light emitter and at least one photodetector could be operated as described above to detect the location, orientation, or some other information about the target and a determination that the target is aligned could be made based on such detected information. Additionally or alternatively, the at least one light emitter and at least one photodetector could be configured to detect some categorical and/or qualitative information about the alignment of the target. For example, the at least one light emitter and at least one photodetector could be configured to detect that the alignment of the target corresponds to one of a discrete set of states, e.g., 'aligned,' 'nearly aligned,' 'not aligned,' 'not aligned in the direction of a second photodetector of the at least one photodetector,' 'not aligned between a second and third light emitter of the at least one light emitter,' etc. That is, in some examples the disposition of the target relative to component(s) of the wearable device could be such that the target is not aligned, and detecting alignment of the at least one light emitter and at least one photodetector relative to the target (820) could include making such a determination. Detecting alignment of the at least one light emitter and at least one photodetector relative to the target (820) could include additional or alternative elements and/or steps.

The method 800 for operating a wearable device could include additional steps relating to a detected alignment of a target and/or other functions of the wearable device. In some examples, the wearable device could include a further sensors configured to detect a property of the target when the target is aligned relative to the at least one light emitter, at least one photodetector, and/or the further sensor, and the method 800 could include detecting the property of the target using the further sensor. Additionally or alternatively, one or more photodetectors of the at least one photodetector could be configured to detect a property of the target when the target is aligned relative to the one or more photodetectors, and the method 800 could include detecting the property of the target using the one or more photodetectors. This could include, responsive to the detection of the alignment of the at least one light emitter and at least one photodetector, using the at least one photodetector to detect light emitted from the target in response to light emitted by the at least one light emitter. Further, one or more of the at least two photodetectors and/or a further sensor could include an energy emitter and operating the at least two photodetectors and/or the further sensor to detect alignment or some other property of the target could include operating the energy emitter to emit some energy (e.g., visible light, infrared light, ultraviolet light, an electromagnetic field, heat).

In some examples, the wearable device could include means to directly or indirectly effect the alignment of the at least one light emitter and at least one photodetector with the target. In some examples, this could include the wearable device including an actuator configured to control the location of the at least one light emitter and at least one photodetector relative to the target. In such examples, the method 800 could further include operating the actuator, relative to the detected alignment of the target relative to the at least one light emitter and at least one photodetector at one or more points in time, to align the at least one light emitter and at least one photodetector with the target. In some examples, this could include the wearable device including an indicator (e.g., a display, a vibrator, a speaker, a buzzer, an electro-haptic stimulator) configured to convey some information about a detected alignment of the target relative to the at least one light emitter and at least one photodetector. In such examples, the method 800 could further include indicating, using the indicator, information detected using the at least one light emitter and at least one photodetector such that a user of the wearable device (e.g., a wearer) can adjust the location of the at least one light emitter, at least one photodetector, and/or other elements of the wearable device to align the at least one light emitter and at least one photodetector relative to the target.

The example method 800 illustrated in FIG. 8 is meant as an illustrative, non-limiting example. Additional or alternative elements of the method and additional or alternative components of the wearable device are anticipated, as will be obvious to one skilled in the art.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device, comprising:
   first and second photodetectors;
   a mount that can mount the wearable device to an external body surface such that the first and second photodetectors are proximate to a target;
   a processor; and
   a non-transitory computer readable medium storing program instructions, wherein the program instructions are executable by the processor to perform operations comprising:
   receiving data from the first and second photodetectors; and
   analyzing the data to determine whether the target is aligned, wherein the target is aligned when the first and second photodetectors detect substantially equal reflected light intensities from the target.

2. The wearable device of claim 1, wherein the target is a portion of subsurface vasculature.

3. The wearable device of claim 1, further comprising:
   an actuator, wherein the operations further comprise operating the actuator to control locations of the first and second photodetectors relative to the target.

4. The wearable device of claim 1, further comprising:
   a user interface, wherein the user interface indicates information relating to adjustment of the wearable device to align the first and second photodetectors relative to the target.

5. The wearable device of claim 1, wherein the operations further comprise operating at least one of the first and second photodetectors to detect whether the wearable device is mounted to the external body surface.

6. The wearable device of claim 1, wherein the external body surface is a location on a wrist.

7. The wearable device of claim 1, further comprising:
   a further sensor, wherein the operations further comprise operating the further sensor to detect a property of the target in response to detecting that the target is aligned.

8. The wearable device of claim 6, wherein the mount comprises a band that can enclose the wrist.

9. The wearable device of claim 7, wherein the further sensor comprises an energy emitter.

10. The wearable device of claim 7, wherein the further sensor is located between the first and second photodetectors.

11. A wearable device, comprising:
    first and second light emitters;
    at least one photodetector;
    a mount that can mount the wearable device to an external body surface such that the first and second light emitters and the at least one photodetector are proximate to a target;

a processor; and a non-transitory computer readable medium storing program instructions, wherein the program instructions are executable by the processor to perform operations comprising:

operating the first and second light emitters;

receiving data from the at least one photodetector; and analyzing the data to determine whether the target is aligned, wherein the target is aligned when the at least one photodetector detects substantially equal reflected light intensities of light emitted from the first and second light emitters and reflected from the target.

12. The wearable device of claim 11, wherein the operations further comprise operating the at least one photodetector to detect a property of the target in response to detecting that the target is aligned.

13. The wearable device of claim 11, further comprising:
an actuator, wherein the operations further comprise operating the actuator to control locations of the light emitters and the at least one photodetector relative to the target.

14. The wearable device of claim 11, further comprising:
a user interface, wherein the user interface indicates information relating to adjustment of the wearable device to align the at least one photodetector relative to the target.

15. The wearable device of claim 11, wherein the target is a portion of subsurface vasculature.

16. The wearable device of claim 11, wherein the at least one photodetector is between the first and second light emitters.

17. The wearable device of claim 11, wherein the external body surface is a location on a wrist.

18. The wearable device of claim 17, wherein the mount comprises a band that can enclose the wrist.

* * * * *